(12) United States Patent
Kashiwagi et al.

(10) Patent No.: US 7,734,013 B2
(45) Date of Patent: Jun. 8, 2010

(54) RADIATION IMAGE CAPTURING APPARATUS AND METHOD OF CONTROLLING RADIATION IMAGE CAPTURING APPARATUS

(75) Inventors: Nobuhiko Kashiwagi, Odawara (JP); Hiroki Nakayama, Aiko-gun (JP)

(73) Assignee: FUJIFILM Corporation, Tokyo (JP)

( * ) Notice: Subject to any disclaimer, the term of this patent is extended or adjusted under 35 U.S.C. 154(b) by 112 days.

(21) Appl. No.: 12/056,066

(22) Filed: Mar. 26, 2008

(65) Prior Publication Data
US 2008/0240346 A1 Oct. 2, 2008

(30) Foreign Application Priority Data
Mar. 26, 2007 (JP) ............................. 2007-079707
Mar. 21, 2008 (JP) ............................. 2008-072754

(51) Int. Cl.
*H05G 1/44* (2006.01)
(52) U.S. Cl. ............................. 378/108; 378/97; 378/37
(58) Field of Classification Search .................... 378/37, 378/62, 97, 108, 110, 112
See application file for complete search history.

(56) References Cited
U.S. PATENT DOCUMENTS
5,485,501 A 1/1996 Aichinger

2003/0165216 A1* 9/2003 Walker et al. ............... 378/108
2004/0156473 A1* 8/2004 Nonaka et al. ............... 378/62

FOREIGN PATENT DOCUMENTS
JP 7-153592 A 6/1995
JP 2000-197624 A 7/2000
JP 2004-154409 A 6/2004

* cited by examiner

*Primary Examiner*—Hoon Song
(74) *Attorney, Agent, or Firm*—Sughrue Mion, PLLC

(57) ABSTRACT

A mammographic system as a radiation image capturing apparatus includes a radiation source for emitting a radiation, AEC sensors for detecting the radiation emitted from the radiation source and acquiring radiation image information for exposure control, a mammary gland position identifier for selecting at least one of the AEC sensors for outputting given radiation dose information based on the radiation dose information acquired by the AEC sensors thereby to identify a mammary gland position as a region of interest of a subject, a weighting coefficient allocator for multiplying output signals from the AEC sensors before the mammary gland position is identified by the mammary gland position identifier, by respective weighting coefficients depending on the installed positions of the AEC sensors, and a radiation source controller for controlling the radiation dose applied from the radiation source to the identified mammary gland position.

15 Claims, 16 Drawing Sheets

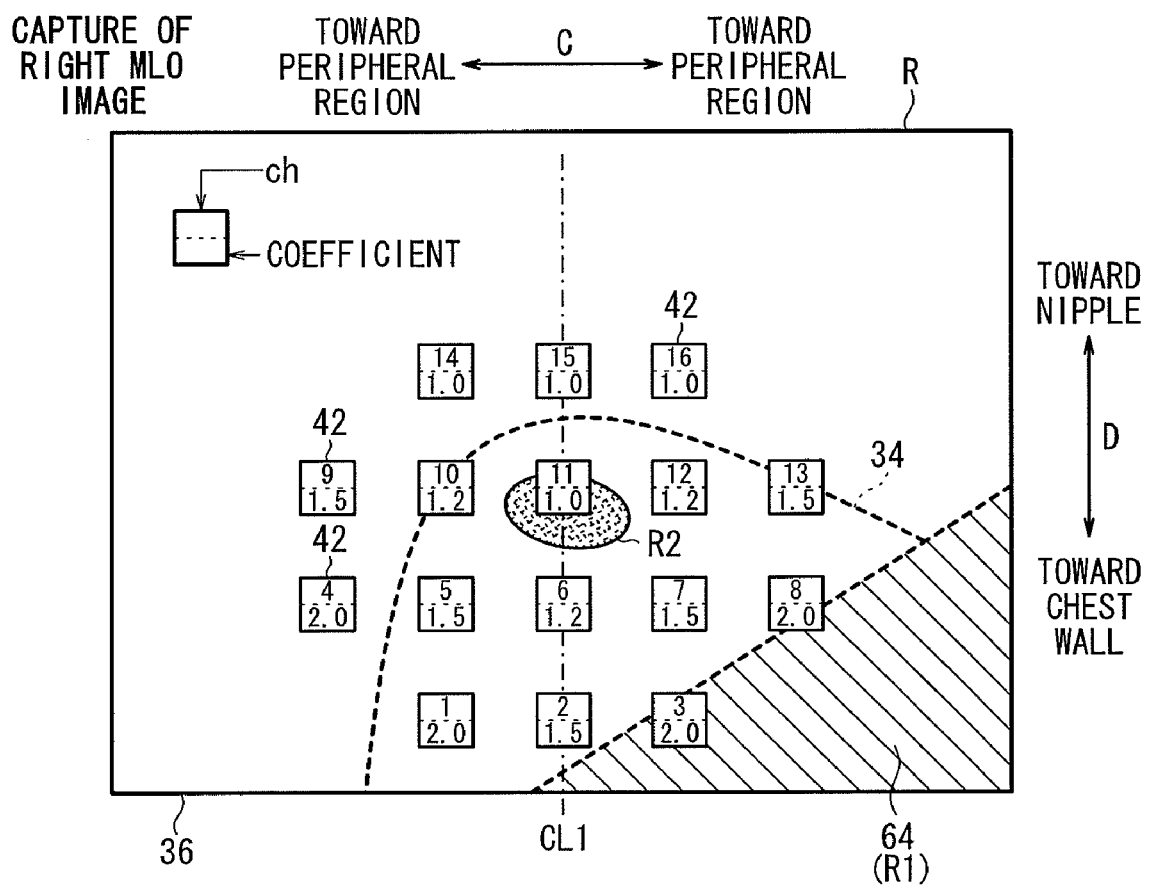

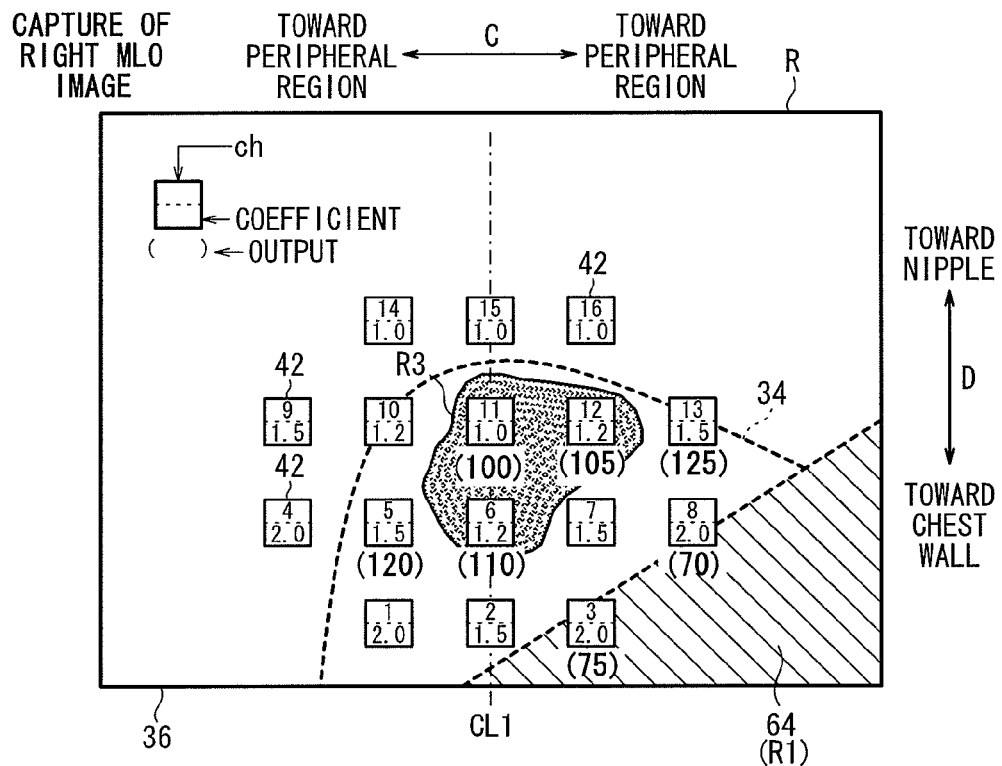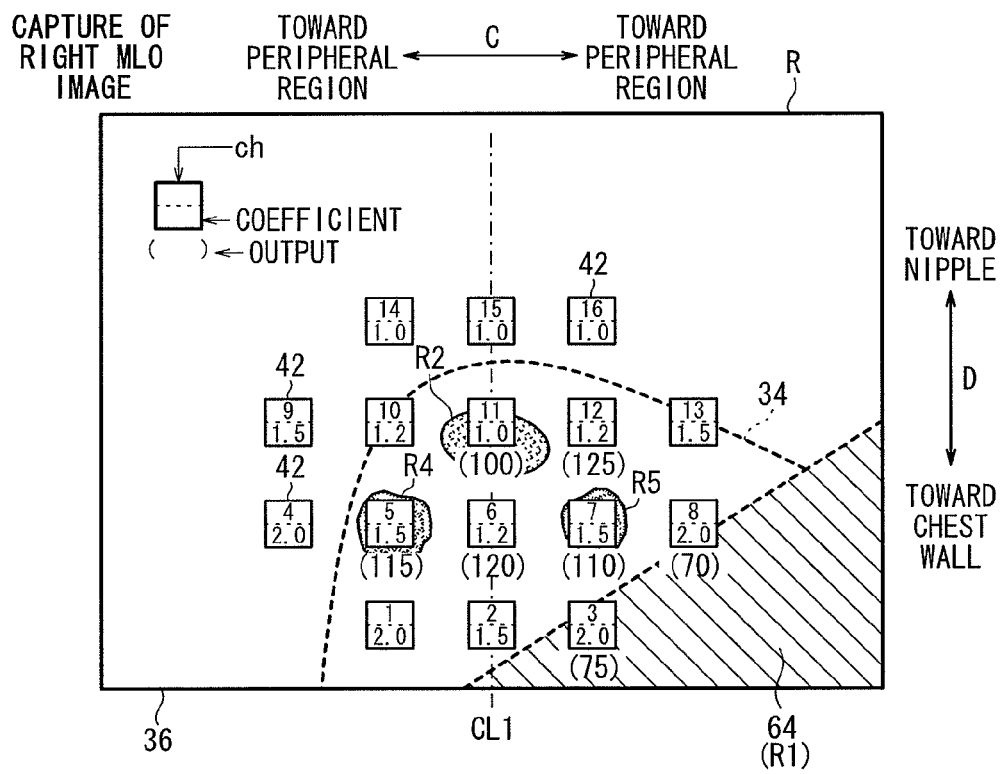

US 7,734,013 B2

RADIATION IMAGE CAPTURING APPARATUS AND METHOD OF CONTROLLING RADIATION IMAGE CAPTURING APPARATUS

CROSS-REFERENCE TO RELATED APPLICATIONS

This application is based upon and claims the benefit of priority from Patent Application No. 2007-079707 filed on Mar. 26, 2007, and Patent Application No. 2008-072754 filed on Mar. 21, 2008, in the Japanese Patent Office, of which the contents are incorporated herein by reference.

BACKGROUND OF THE INVENTION

1. Field of the Invention

The present invention relates to a radiation image capturing apparatus for acquiring radiation image information of a subject, and a method of controlling such a radiation image capturing apparatus.

2. Description of the Related Art

In the medical field, there have widely been used radiation image capturing apparatus which apply a radiation emitted from a radiation source to a subject (patient), detect the radiation that has passed through the subject with a radiation detector, and record radiation image information based on the detected radiation.

The radiation image capturing apparatus of the type described above are required to achieve a good level of radiation image quality while minimizing the radiation dose applied to the subject. In order to acquire appropriate radiation image information of a region of interest (ROI) of the subject, it is necessary to establish an exposure control condition for applying a desired dose of radiation to the region of interest. There has been proposed a radiation image capturing apparatus including an AEC (Automatic Exposure Control) system for controlling a radiation dose emitted from the radiation source based on a detected radiation dose that has passed through the subject.

One known radiation image capturing apparatus is a mammographic system used for breast cancer screening. The mammographic system comprises an image capturing base housing a panel-like solid-state detector for supporting a subject's breast to be imaged, a compression plate disposed in confronting relation to the image capturing base for compressing the breast against the image capturing base, and a radiation source for applying a radiation through the compression plate to the breast.

The subject's breast comprises a mammary gland region and a fat region. In terms of breast cancer screening, the region of interest is the mammary gland region because it is highly susceptible to breast cancer. While the mammary gland region has a large coefficient of absorption of radiations, the fat region has a small coefficient of absorption of radiations and absorbs almost no radiations. In order to acquire appropriate radiation image information of the mammary gland region, it is necessary to set suitable exposure control conditions based on the mammary gland region for applying a desired dose of radiation to the mammary gland region. The exposure control conditions include a tube voltage, a tube current, a radiation exposure time, etc. to be established for the radiation source. Of these exposure control conditions, the tube current and the radiation exposure time are the most important conditions for determining a dose of radiation to be applied to the subject.

Some mammographic systems include a radiation dose information detector for AEC housed in the image capturing base, the radiation dose information detector being used such that a small output range thereof is identified as representing the region of a high mammary gland density (see Japanese laid-open patent publication No. 2000-197624 and Japanese laid-open patent publication No. 7-153592).

When a medio-lateral oblique (MLO) image, for example, is to be taken by the mammographic system, since the radiation is applied obliquely to the subject, the breast muscle comes into the radiation detection area. Generally, the breast muscle tends to have a greater coefficient of absorption of radiations than that of the mammary gland region.

Therefore, the breast muscle is represented by a lower output range of the radiation dose information detector than the mammary gland region is. As a result, the breast muscle may possibly be identified as the region of interest when the region of a high mammary gland density needs to be identified as the region of interest. If the breast muscle is identified as the region of interest, then it is difficult to obtain appropriate radiation image information of the mammary gland region, possibly making it impossible to generate a desired radiation image of the breast.

SUMMARY OF THE INVENTION

It is a general object of the present invention to provide a radiation image capturing apparatus which is capable of accurately selecting a radiation dose measuring position representative of a region of interest from a plurality of positions for measuring radiation dose information and hence of generating a desired radiation image of the region of interest, and a method of controlling such a radiation image capturing apparatus.

According to an aspect of the present invention, there is provided a method of controlling a radiation image capturing apparatus for capturing a radiation image of a subject, comprising the steps of applying a radiation from a radiation source to a region to be imaged of the subject, detecting a dose of the radiation which has passed through the region to be imaged at a plurality of radiation dose measuring positions, multiplying respective pieces of radiation dose information measured at the radiation dose measuring positions by respective weighting coefficients depending on the radiation dose measuring positions for selecting one or more of the radiation dose measuring positions based on the radiation dose information multiplied by the weighting coefficients, and determining an exposure control condition for the radiation from the radiation source based on the radiation dose information measured at the selected one or more radiation dose measuring positions.

In the aspect of the present invention, the step of multiplying respective pieces of the radiation dose information may comprise a first step of multiplying respective pieces of radiation dose information measured at the radiation dose measuring positions by respective weighting coefficients depending on the radiation dose measuring positions for selecting one or more predetermined radiation dose measuring positions and a second step of comparing the multiplied radiation dose information with radiation dose information before multiplied in the first step, for selecting one or more radiation dose measuring positions having radiation dose information within a predetermined range, and wherein the step of determining the exposure control condition for the radiation comprises the step of determining the exposure control condition for the radiation from the radiation source based on respective pieces of radiation dose information at respective radiation dose measuring positions that have been selected in the first step and said second step. In this case, the predetermined range in the second step is variable.

According to another aspect of the present invention, there is also provided an apparatus for capturing a radiation image, comprising a radiation source for applying a radiation to a region to be imaged of a subject, a radiation dose information detector for detecting a dose of the radiation which has passed through the region to be imaged at a plurality of radiation dose measuring positions, and acquiring respective pieces of radiation dose information for exposure control at the radiation dose measuring positions, weighting coefficient allocating means for multiplying the respective pieces of the radiation dose information measured at the radiation dose measuring positions by respective weighting coefficients depending on the radiation dose measuring positions, measuring position selecting means for selecting one or more of the radiation dose measuring positions based on the pieces of the radiation dose information multiplied by the weighting coefficients, and radiation source control means for controlling the dose of the radiation emitted from the radiation source based on the pieces of the radiation dose information measured at the one or more radiation dose measuring positions which are selected by the measuring position selecting means.

According to the present invention, for selecting one of the radiation dose measuring positions at which the radiation dose information is detected, the respective pieces of the radiation dose information measured at the radiation dose measuring positions are multiplied by weighting coefficients. Consequently, those radiation dose measuring positions which prevent the region of interest from being accurately identified, e.g., radiation dose measuring positions overlapping a breast muscle in capturing an MLO image on a mammographic system, are effectively prevented from being selected. Rather, a desired one of the radiation dose measuring positions can accurately be selected to allow a desired radiation image of the subject to be reliably acquired.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 6 is a schematic plan view showing the manner in which the breast is held on the image capturing base for capturing a right MLO image thereof;

FIG. 8A is a schematic plan view showing output signals from AEC sensors before they are multiplied by weighting coefficients when a region where the mammary gland density is high covers a wide range;

FIG. 8B is a schematic plan view showing output signals from AEC sensors before they are multiplied by weighting coefficients when regions where the mammary gland density is high are scattered;

DESCRIPTION OF THE PREFERRED EMBODIMENTS

A radiation image capturing apparatus and a method of controlling such a radiation image capturing apparatus according to preferred embodiments of the present invention will be described in detail below with reference to the accompanying drawings.

Figure 1:
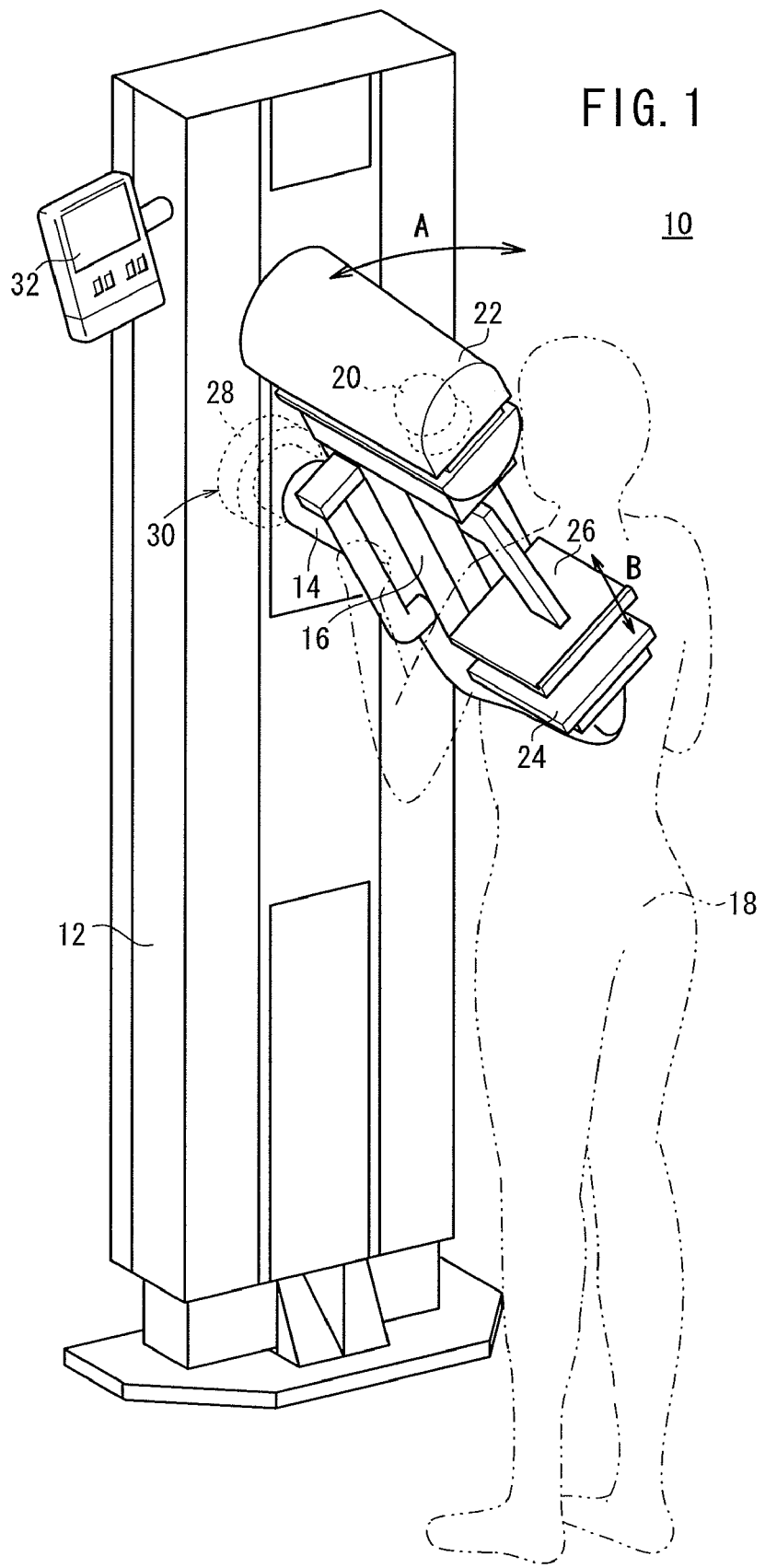
FIG. 1 is a perspective view of a mammographic system as a radiation image capturing apparatus according to an embodiment of the present invention.

FIG. 1 shows in perspective a mammographic system 10 as a radiation image capturing apparatus according to an embodiment of the present invention. In FIG. 1, the mammographic system 10 is shown as being in an operative position for capturing a medio-lateral oblique (MLO) image of a subject by applying a radiation obliquely to the subject. Though the mammographic system 10 will be described below as the radiation image capturing apparatus according to the embodiment of the present invention, the present invention is not limited to the mammographic system 10.

As shown in FIG. 1, the mammographic system 10 includes an upstanding base 12, an arm 16 fixed to a horizontal swing shaft 14 disposed substantially centrally on the base 12, a radiation source housing unit 22 storing a radiation source 20 for applying a radiation to a breast, as a region to be imaged, of a subject 18 and fixed to an upper end of the arm 16, an image capturing base 24 disposed in confronting relation to the radiation source housing unit 22 and fixed to a lower end of the arm 16, and a compression plate 26 for compressing and holding the breast against the image capturing base 24. The swing shaft 14 can be rotated about its own axis by a drive motor 28 housed in the base 12. The swing shaft 14 and the drive motor 28 jointly make up a rotating mechanism 30 for rotating the arm 16.

When the arm 16, to which the radiation source housing unit 22 and the image capturing base 24 are secured, is angularly moved about the swing shaft 14 by the drive motor 28 in the directions indicated by the arrow A, an image capturing direction with respect to the breast of the subject 18 is adjusted. While the arm 16 is being angularly moved, the radiation source 20 and the image capturing base 24 are maintained in their relative positional relationship. The compression plate 26 that is coupled to the arm 16 is disposed between the radiation source housing unit 22 and the image capturing base 24. The compression plate 26 is vertically displaceable along the arm 16 in the directions indicated by the arrow B.

To the base 12, there is connected a display control panel 32 for displaying image capturing information including an image capturing region, an image capturing direction, etc. of the subject 18 detected by the mammographic system 10, the ID information of the subject 18, etc., and setting these items of information, if necessary.

Figure 2:
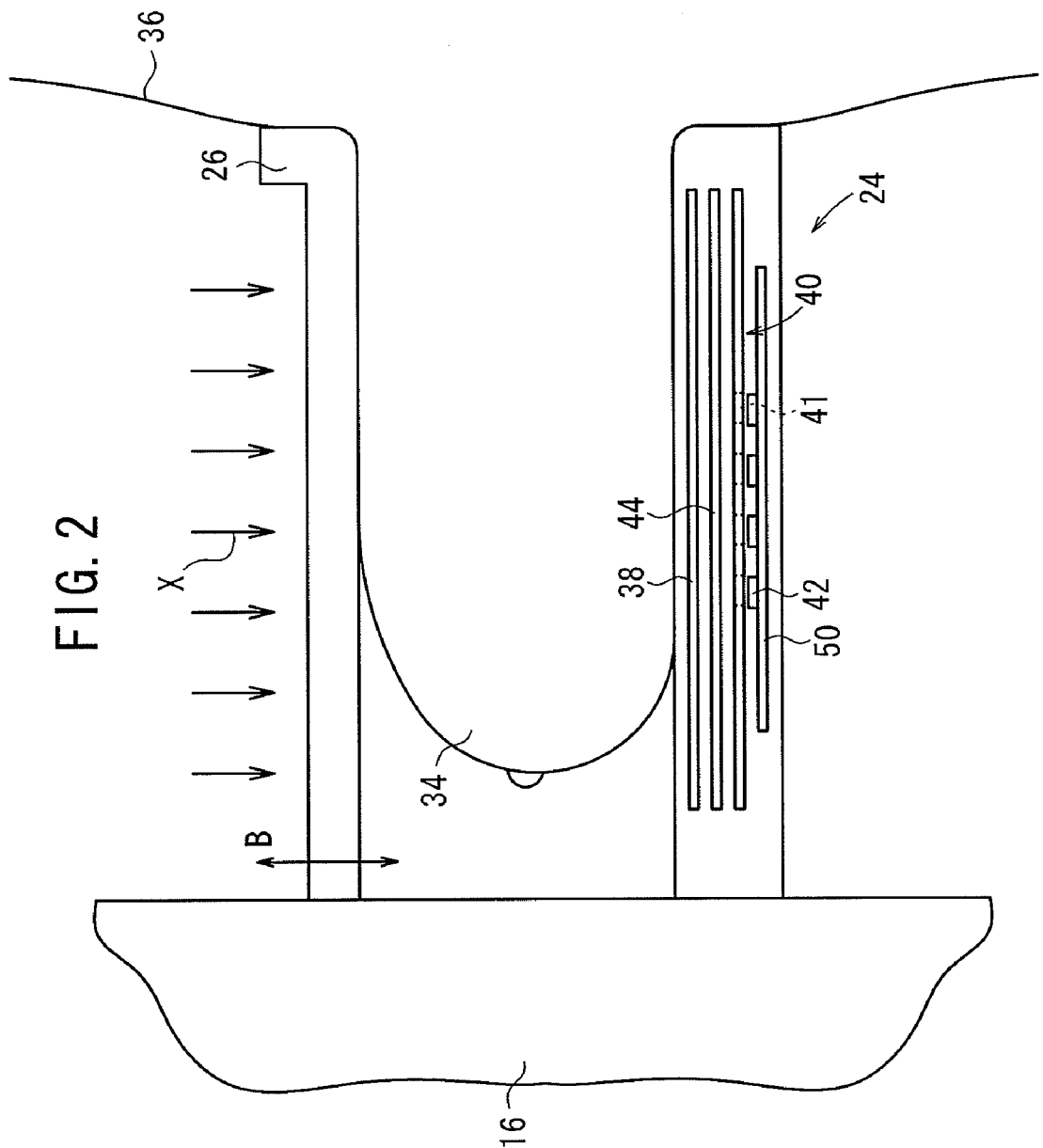
FIG. 2 is a fragmentary vertical elevational view, partly in cross section, showing internal structural details of an image capturing base of the mammographic system shown in FIG. 1.

FIG. 2 shows internal structural details of the image capturing base 24 of the mammographic system 10. In FIG. 2, the breast, denoted by 34, of the subject 18 is shown as being placed between the image capturing base 24 and the compression plate 26. The reference numeral 36 represents the chest wall of the subject 18.

The image capturing base 24 houses therein a solid-state detector (image sensor) 38 for storing radiation image information captured based on the radiation X that has been emitted from the radiation source 20 housed in the radiation source housing unit 22, and outputting the stored radiation image information as an electric signal, and a reading light source 44 for applying reading light to the solid-state detector 38 to read the radiation image information stored in the solid-state detector 38. The image capturing base 24 also houses therein a plurality of radiation dose information detectors (hereinafter referred to as AEC sensors 42) for detecting the radiation dose of the radiation X that has passed through the breast 34 and the solid-state detector 38 in order to determine exposure (irradiation) control conditions for the radiation X, and an erasing light source 40 for applying erasing light to the solid-state detector 38 to remove unwanted electric charges stored in the solid-state detector 38.

The solid-state detector 38 comprises a direct-conversion, light-reading radiation solid-state detector.

The solid-state detector 38 stores radiation image information based on the radiation X that has passed through the breast 34 as an electrostatic latent image, and generates an electric current depending on the electrostatic latent image when the solid-state detector 38 is scanned by the reading light applied from the reading light source 44.

The solid-state detector 38 may be a detector as disclosed in Japanese laid-open patent publication No. 2004-154409, for example. More specifically, the solid-state detector 38 comprises a laminated assembly of a first electrically conductive layer disposed on a glass substrate for passing the radiation X therethrough, a recording photoconductive layer for generating electric charges upon exposure to the radiation X, a charge transport layer which acts substantially as an electric insulator with respect to latent image polarity electric charges developed in the first electrically conductive layer and which acts substantially as an electric conductor with respect to transport polarity charges which are of a polarity opposite to the latent image polarity electric charges, a reading photoconductive layer for generating electric charges and making itself electrically conductive upon exposure to the reading light, and a second electrically conductive layer which is permeable to the radiation X. An electric energy storage region is provided in the interface between the recording photoconductive layer and the charge transport layer.

Each of the first electrically conductive layer and the second electrically conductive layer provides an electrode. The electrode provided by the first electrically conductive layer comprises a two-dimensional flat electrode. The electrode provided by the second electrically conductive layer comprises a plurality of linear electrodes spaced at a predetermined pixel pitch for detecting the radiation image information of the radiation image to be recorded as an image signal. The linear electrodes are arranged in an array along a main scanning direction, and extend in an auxiliary scanning direction perpendicular to the main scanning direction.

The reading light source 44 includes, for example, a line light source comprising a linear array of LED chips and an optical system for applying a line of reading light emitted from the line light source to the solid-state detector 38. The linear array of LED chips extends perpendicularly to the direction in which the linear electrodes of the second electrically conductive layer of the solid-state detector 38 extend. The line light source moves along the directions, i.e., the directions indicated by the arrow C in FIG. 3, in which the linear electrodes extend to expose and scan the entire surface of the solid-state detector 38.

Figure 3:
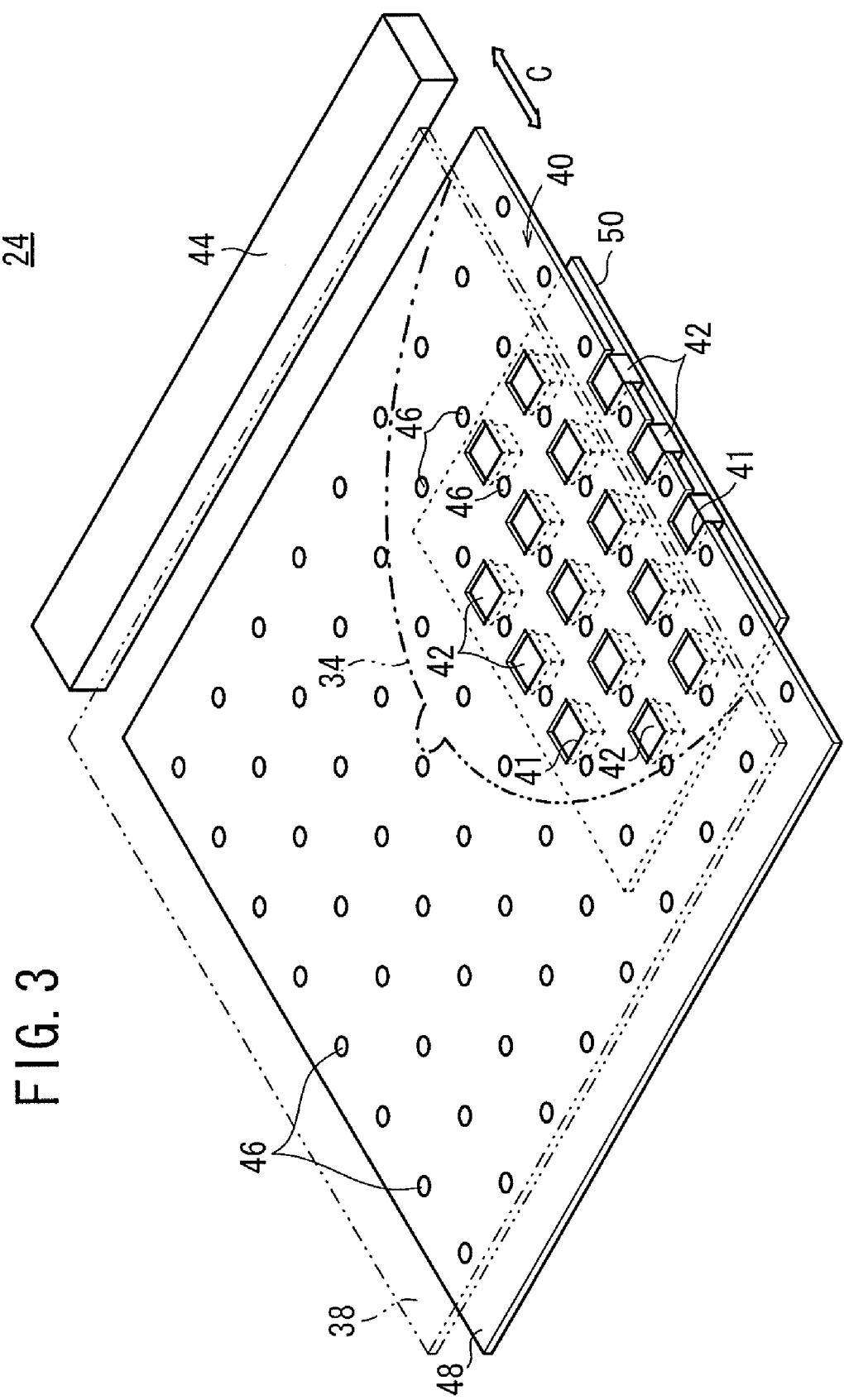
FIG. 3 is a perspective view, partly omitted from illustration, of the internal structural details of the image capturing base shown in FIG. 2.

As shown in FIG. 3, the erasing light source 40 comprises a plurality of LED chips 46 which can emit and quench light in a short period of time and which have very short persistence. The LED chips 46 are arrayed in a matrix and mounted on a panel 48. The panel 48 is mounted in the image capturing base 24 parallel to the solid-state detector 38.

As shown in FIGS. 2 and 3, the plurality of (16 in the present embodiment) AEC sensors 42 are mounted on a sensor board 50 and oriented from respective holes 41 defined in the panel 48 toward the solid-state detector 38. The AEC sensors 42 are surrounded by respective rectangular tubular members (not shown) which extend from the holes 41 toward the AEC sensors 42 along the direction of the radiation X emitted from the radiation source 20.

The AEC sensors 42 are arrayed on the sensor board 50 so as to correspond positionally to the breast 34 which is positioned on the image capturing base 24 (see FIG. 3).

Figure 4:
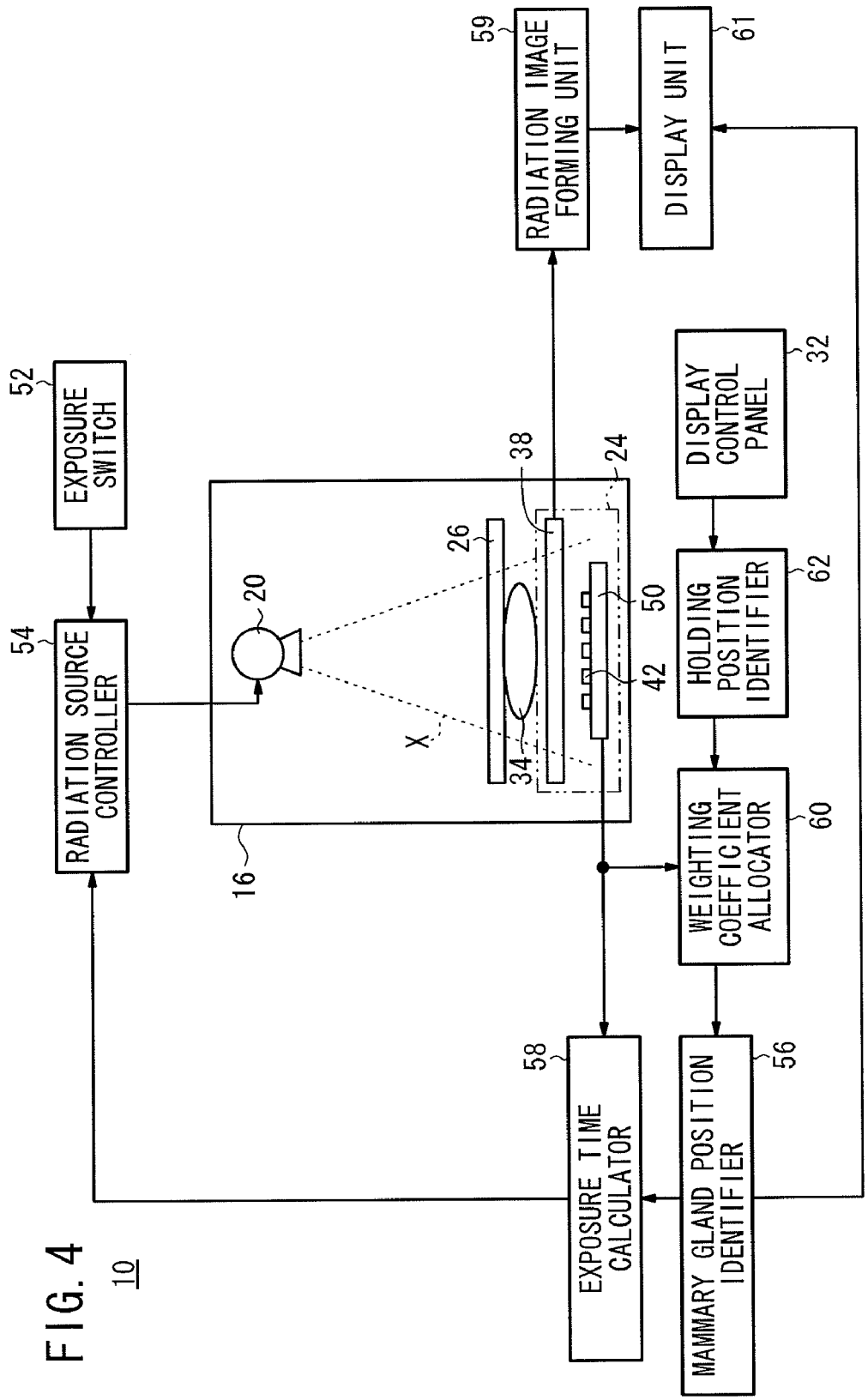
FIG. 4 is a block diagram of a control circuit of the mammographic system shown in FIG. 1.

As shown in FIG. 4, a control circuit of the mammographic system 10 includes a radiation source controller (radiation source control means) 54 housed in the radiation source housing unit 22 for controlling the radiation source 20 to emit the radiation X when an exposure switch 52 is triggered, a mammary gland position identifier (measuring position selecting means) 56 for identifying the mammary gland position (region of interest) of the breast 34 based on the radiation dose of the radiation X detected by the AEC sensors 42 as the radiation dose information detectors, and an exposure time calculator 58 for calculating an appropriate exposure time in which to emit the radiation X from the radiation source 20 based on the radiation dose per unit time of the radiation X detected by the AEC sensors 42, and supplying the calculated exposure time as an exposure control condition to the radiation source controller 54.

The control circuit of the mammographic system 10 also includes a radiation image forming unit 59 for forming a radiation image based on the radiation image information detected by the solid-state detector 38, and a display unit 61 for displaying the generated radiation image. The solid-state detector 38 thus functions as a radiation image generating means for detecting a radiation emitted from the radiation source 20 and generating a radiation image. The display unit 61 also displays positional information representing the mammary gland position identified by the mammary gland position identifier 56, e.g., an image representing AEC sensors 42, in overlapping relation to the radiation image.

The control circuit of the mammographic system 10 further includes a weighting coefficient allocator (weighting coefficient allocating means) 60 for multiplying the output signals (radiation dose information) from the AEC sensors 42 by given weighting coefficients, and a holding position identifier (holding position identifying means) 62 for identifying (detecting) the holding position in which the breast 34 is held on the image capturing base 24 and supplying the identified holding position to the weighting coefficient allocator 60.

The mammographic system 10 according to the present embodiment is thus constructed as an automatic exposure control system for identifying a region of interest of the breast 34 with the mammary gland position identifier 56 based on the radiation dose detected by the AEC sensors 42, and controlling the radiation source 20 with the radiation source controller 54.

The mammographic system 10 according to the present embodiment is basically constructed as described above. Operation of the mammographic system 10 will be described below.

Using a console, an ID card, etc., not shown, the operator, who is typically a radiological technician, sets ID information, an image capturing process, etc. for the subject 18. The ID information includes information as to the name, age, sex, etc. of the subject 18, and can be acquired from an ID card owned by the subject 18. If the mammographic system 10 is connected to a network, the ID information can be acquired from a higher-level apparatus through the network. The image capturing process represents information including a region to be imaged that is specified by the doctor, an image capturing direction that is specified by the doctor, etc., and can acquired from a higher-level apparatus through the network or entered through the console by the operator. These items of information can be displayed on the display control panel 32 of the mammographic system 10.

Then, the operator places the mammographic system 10 into a certain state according to the specified image capturing process. For example, the breast 34 may be imaged as a cranio-caudal (CC) image taken from above, a medio-lateral (ML) image taken outwardly from the center of the chest, or a medio-lateral oblique (MLO) image taken from an oblique view. Depending on the information of a selected one of these image capturing directions, the operator turns the arm 16 about the swing shaft 14.

Operation of the mammographic system 10 which is in the operative position for taking a medio-lateral oblique (MLO) image of the breast 34, as shown in FIG. 1, will be described below mainly with reference to FIGS. 4 through 8.

Figure 5:
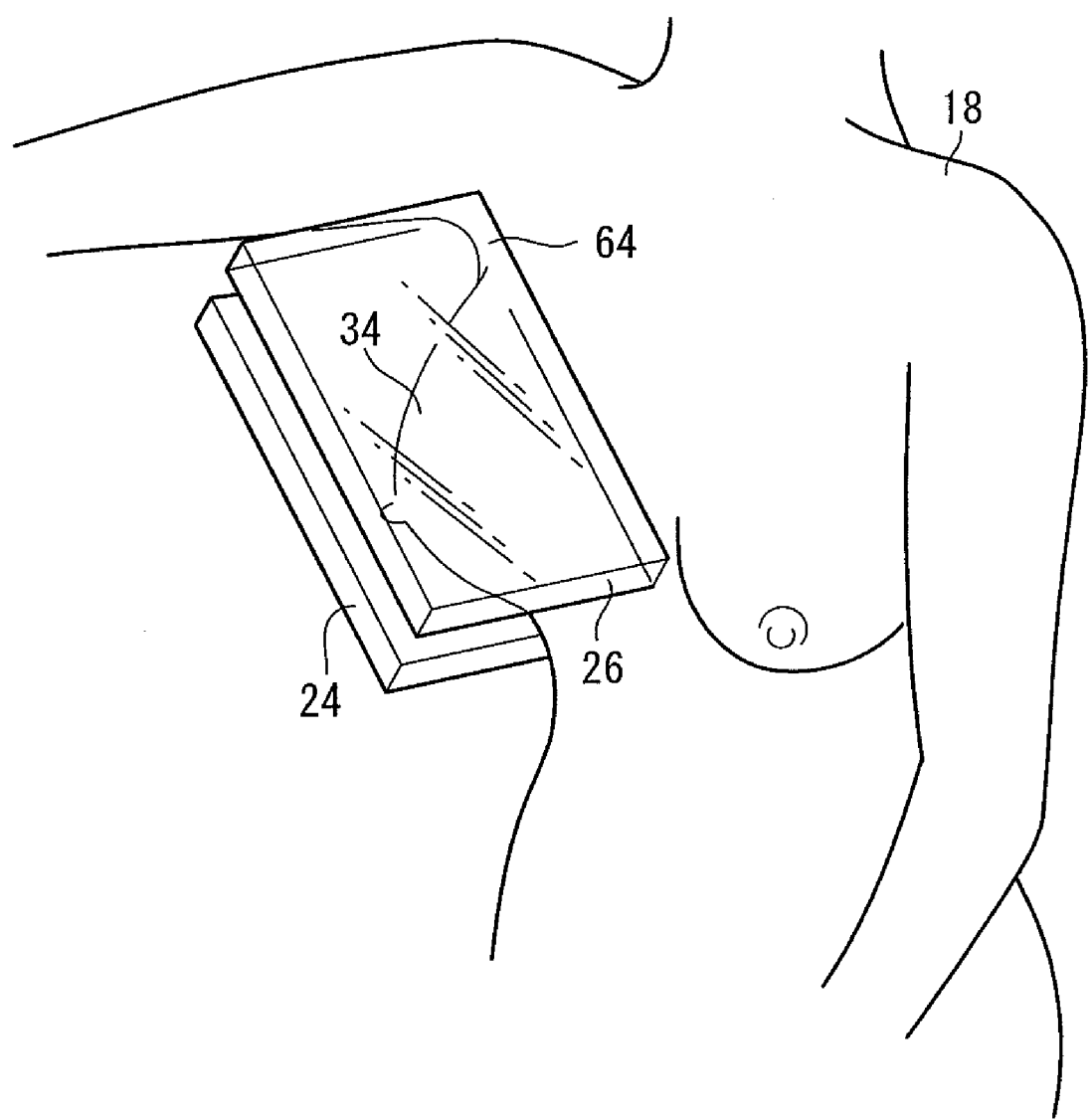
FIG. 5 is a perspective view, partly omitted from illustration, showing the manner in which a right MLO image of a breast is captured.

For capturing a right MLO image of the right breast 34 as shown in FIGS. 1 and 5, the arm 16 is turned a predetermined angle about the swing shaft 14 and set to a predetermined angular position. Then, the operator positions the right breast 34 of the subject 18 with respect to the mammographic system 10. Specifically, the operator places the right breast 34 on the placement surface of the image capturing base 24, and thereafter lowers the compression plate 26 toward the image capturing base 24 to hold the breast 34 between the image capturing base 24 and the presser plate 26, as shown in FIGS. 2 and 5. More specifically, the operator holds an outer side of the right breast 34, which faces the right arm of the subject 18, against the image capturing base 24, and presses the compression plate 26 against an inner side of the right breast 34, which faces the left breast 34, thereby holding the right breast 34 between the image capturing base 24 and the compression plate 26.

In this operative position for taking a medio-lateral oblique (MLO) image of the right breast 34, the right breast 34 and also a nearby breast muscle 64 of the subject 18 are usually held between the image capturing base 24 and the compression plate 26 (see FIG. 5).

After the above preparatory operation has been completed, the operator operates the mammographic system 10 to start to take a radiation image of the breast 34.

First, the mammographic system 10 operates in a mode (hereinafter referred to as "pre-exposure mode") for determining an exposure control condition for the region of interest (mammary gland region) by setting the radiation dose of the radiation X to be applied to the breast 34 to a low level, and then operates in a mode (hereinafter referred to as "main exposure mode") for applying the radiation X at a radiation dose according to the determined exposure control condition to capture a radiation image of the breast 34.

The radiation source controller 54 controls the tube current supplied to the radiation source 20 to set the radiation dose per unit time to a low level, and the radiation source 20 applies the radiation X at the low radiation dose to the breast 34.

The AEC sensors 42 detect the radiation dose of the radiation X that has passed through the compression plate 26, the breast 34, and the solid-state detector 38, and supply the detected radiation dose to the mammary gland position identifier 56. The mammary gland position identifier 56 calculates a radiation dose per unit time from the radiation dose of the radiation X detected at each given sampling time by the AEC sensors 42, and determines a mammary gland position based on the calculated radiation dose. Specifically, the mammary gland position identifier 56 selects one of the AEC sensors 42 which outputs a minimum radiation dose and identifies a mammary gland position based on the selected AEC sensor 42. In this manner, the mammary gland position identifier 56 detects a radiation dose measuring position where the mammary gland density is the highest as a mammary gland position (region of interest).

FIG. 6 is a schematic plan view showing the manner in which the breast 34 is held on the image capturing base 24 for capturing a right MLO image thereof. As shown in FIG. 6, not only the breast 34 but also the breast muscle 64 are positioned on some of the AEC sensors 42. Each of the sensors 42 shown in FIG. 6 is represented by a square shape containing an upper numeral which indicates the channel number of the AEC sensor 42 and a lower numeral which indicates a weighting coefficient by which the output signal of the AEC sensor 42 is to be multiplied. The channel number is assigned to each AEC sensor 42 for the convenience of illustration. For example, the AEC sensor 42 with the channel number 1 (ch1) will be referred to as AEC sensor ch1, and the AEC sensor 42 with the channel number 2 (ch2) as AEC sensor ch2.

The radiation X that passes through the breast 34 is not significantly absorbed by the fat region, but is greatly absorbed by the mammary gland region and the breast muscle 64, particularly most greatly by the breast muscle 64. Therefore, of the AEC sensors 42, AEC sensors ch3, ch8 which are positioned in a region (shown hatched as indicated by R1 in FIG. 6) overlapping the breast muscle 64 produce output signals representing the minimum radiation dose. Therefore, unless these output signals are appropriately weighted, the mammary gland position identifier 56 may possibly tend to identify the position of the AEC sensor ch3 or ch8 overlapping the breast muscle 64 as a mammary gland position, but may fail to identify a region (shown stippled as indicated by R2 in FIG. 6) where the mammary gland density is actually high as a mammary gland position (radiation dose measuring position).

According to the present embodiment, when the mammary gland position identifier 56 is to identify a mammary gland position, the radiation dose information output from the AEC sensors 42 is introduced into the weighting coefficient allocator 60. Based on the positions where the AEC sensors 42 are installed, i.e., the positions where the radiation dose information is measured, the weighting coefficient allocator 60 multiplies the output signals (radiation dose information) from the respective AEC sensors 42 by respective preset (stored) weighting coefficients. For example, as shown in FIG. 6, the weighting coefficient allocator 60 multiplies the output signal from the AEC sensor ch1 by a weighting coefficient of 2.0, the output signal from the AEC sensor ch1 by a weighting coefficient of 1.0, and the output signals from the other AEC sensors by respective weighting coefficient.

As shown in FIG. 6, the weighting coefficients by which the output signals from the AEC sensors are to be multiplied are established such that they are stepwise greater from those AEC sensors 42 (AEC sensors ch2, ch6, ch11, ch15) installed on a central line CL1 at the center of the breast 34 toward outer peripheral AEC sensors 42 in the directions indicated by the arrow C along the chest wall 36. The weighting coefficients are also established such that they are stepwise smaller from the chest wall 36 toward the nipple of the breast 34 in the direction indicated by the arrow D.

Stated otherwise, for capturing an MLO image based on the radiation dose information detected in a radiation detecting region R (see FIG. 6), the weighting coefficient allocator 60 multiplies the output signals from those AEC sensors 42 which belong to or are near the region R1 of the radiation detecting region R, by a larger weighting coefficient, or multiplies output signals from those AEC sensors 42 which belong to or are near the region R2 of the radiation detecting region R, by smaller weighting coefficients.

Figure 7A:
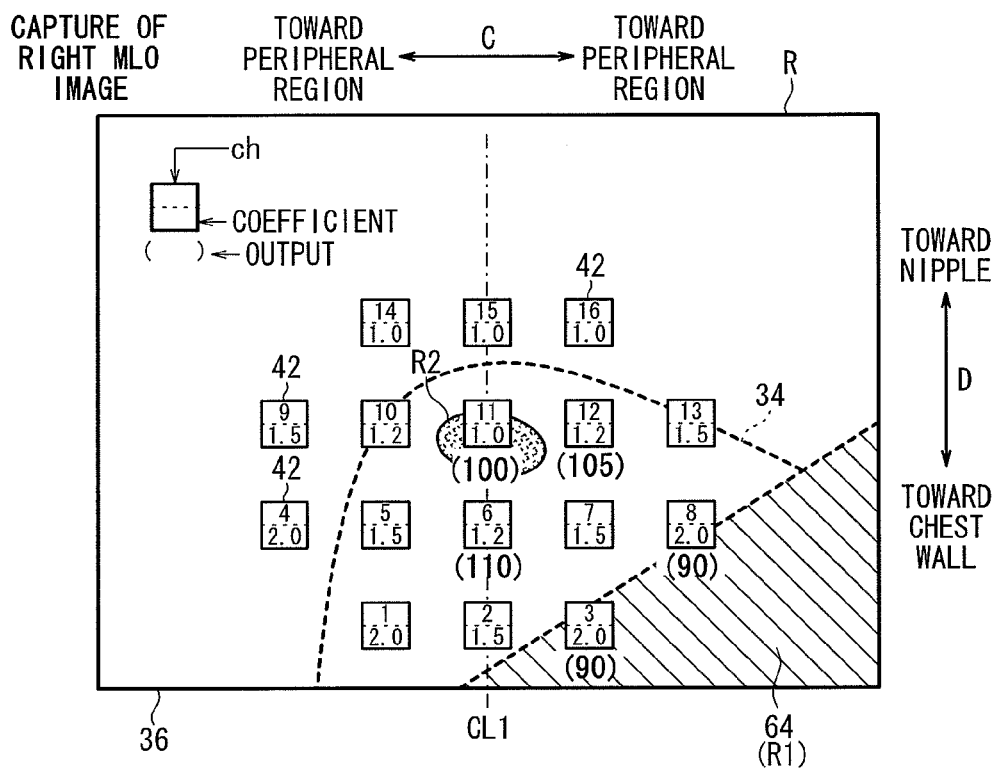
FIG. 7A is a schematic plan view showing output signals from AEC sensors before they are multiplied by weighting coefficients.
Figure 7B:
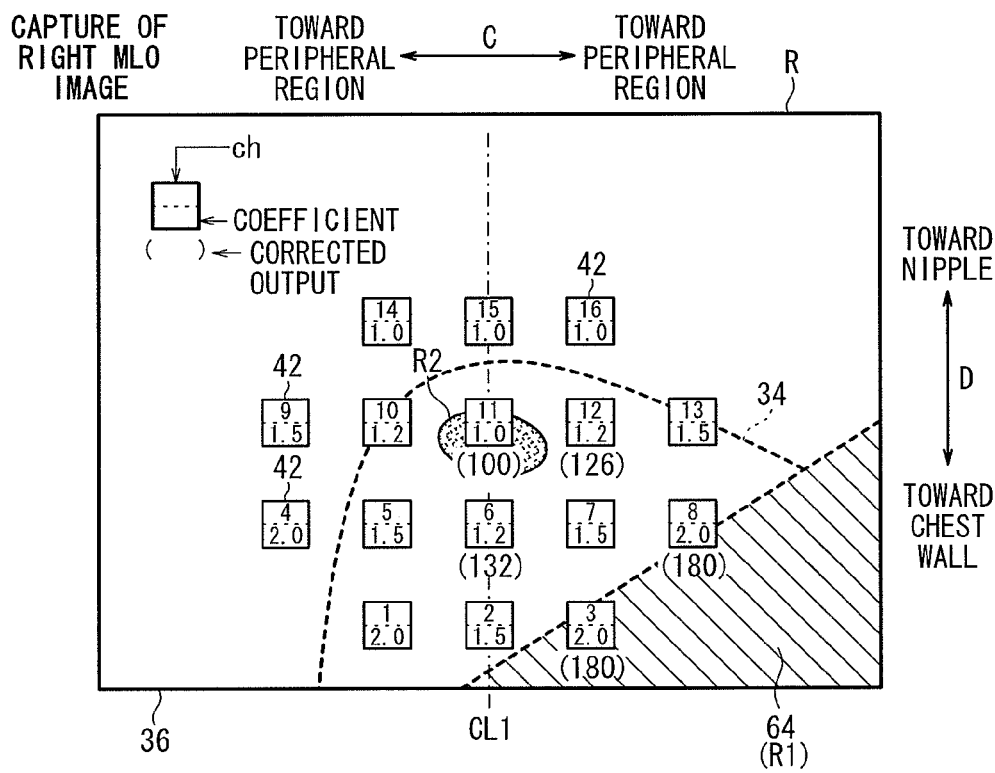
FIG. 7B is a schematic plan view showing output signals from AEC sensors which have been multiplied by weighting coefficients.

For example, as shown in FIG. 7A, it is assumed that the output signal (e.g., a current (mA)) representing the radiation dose information detected by the AEC sensor ch11 positioned in the region R2 where the mammary gland density is high is indicated by 100, the output signals representing the radiation dose information detected by the AEC sensors ch6, ch12 near the AEC sensor ch11 are indicated by 115, 120, respectively, and the output signals representing the radiation dose information detected by the AEC sensors ch3, ch8 positioned in the region R1 overlapping the breast muscle 64 are indicated by 75, 70, respectively. The weighting coefficient allocator 60 multiplies these output signals by respective weighting coefficients established depending on the positions of those AEC sensors 42. As a result, as shown in FIG. 7B, the output signal from the AEC sensor ch11 positioned in the region R2 is corrected (processed) into 100, the output signals from the AEC sensors ch6, ch12 near the AEC sensor ch11 are corrected (processed) into 138, 144, respectively, and the output signals from the AEC sensors ch3, ch8 positioned in the region R1 are corrected (processed) into 150, 140, respectively. The corrected output signals are then supplied to the mammary gland position identifier 56.

The mammary gland position identifier 56 selects the AEC sensor 42, i.e., the AEC sensor ch11, whose output signal represents the minimum radiation dose, among the corrected output signals (radiation dose information) supplied from the weighting coefficient allocator 60, and identifies the position of the AEC sensor ch11 as the mammary gland position. The mammary gland position identifier 56 can thus reliably select the AEC sensor ch11 positioned in the region R2 where the mammary gland density is high as shown in FIG. 6, and hence can accurately detect the position where the mammary gland density is highest as the mammary gland position (radiation dose measuring position).

As described above, the weighting coefficient allocator 60 multiplies the output signals from the AEC sensors 42 by weighting coefficients which are established such that the mammary gland position identifier 56 preferentially selects one of the AEC sensors 42 which is positioned more toward the center of the breast 34 than the peripheral region thereof and which is positioned more toward the nipple than the chest wall 36. Consequently, the mammary gland position identifier 56 is effectively prevented from erroneously selecting the positions of the AEC sensors 42 in the region R1 overlapping the breast muscle 64 as the mammary gland position (region of interest).

As described above, the mammary gland position identifier 56 selects only one AEC sensor 42, e.g., AEC sensor ch11, whose output signal represents the minimum radiation dose, among the corrected output signals of the AEC sensors 42 which are supplied from the weighting coefficient allocator 60, to identify a mammary gland position. However, the mammary gland position identifier 56 may select a plurality of AEC sensors 42 and identify a region near a mammary gland position based on the average value (average output signal) or the median (median output signal) of the output signals from the selected AEC sensors 42.

The mammary gland position identifier 56 selects a plurality of AEC sensors 42 to identify a region near a mammary gland position using the average value or the median. Thus, it is possible to more accurately and flexibly deal with various measurement cases depending on differences of breasts 34 among individuals, for example, cases in which a region where the mammary gland density is high is wide enough to cover a plurality of AEC sensors 42 (see FIG. 8A), or in which regions where the mammary gland density is high are scattered (see FIG. 8B).

For example, as shown in FIG. 8A, when the region R3 where the mammary gland density is high covers a wide range, the mammary gland position identifier 56 first selects the AEC sensor ch11 which outputs the minimum radiation dose after correction by the weighting coefficient allocator 60. Specifically, as seen from FIG. 8A, the AEC sensor ch 11 has an actual output (actual output value before weighting) of 100, an output after correction of 100, and the minimum output after correction among outputs of all AEC sensors 42.

Next, the mammary gland position identifier 56 selects every AEC sensor 42 whose actual output falls within ±20% (80 to 120) of the actual output of the selected AEC sensor ch11 which outputs the minimum radiation dose. Specifically, in this case, since the actual output of the AEC sensor ch11 indicates 100, the AEC sensor ch5 (actual output: 120), ch6 (actual output: 110) and ch12 (actual output: 105) are selected.

Then, the mammary gland position identifier 56 averages the actual outputs of the selected AEC sensors ch11, ch5, ch6 and ch12, and supplies the average value {108.75=(100+ 120+110+105)/4} as the final data, to the exposure time calculator 58. As described above, the median of the selected AEC sensors 42 may be used as the final data.

As shown in FIG. 8B, when the regions where the mammary gland density is high are scattered as the regions R2, R4 and R5, as with the case shown in FIG. 8A, the mammary gland position identifier 56 first selects the AEC sensor ch11 which outputs the minimum radiation dose after correction by the weighting coefficient allocator 60. Next, the mammary gland position identifier 56 selects the AEC sensors ch5, ch6, ch7 and ch12 whose actual outputs fall within ±20% of the actual output of the selected AEC sensor ch11, and supplies the average value or the median based on the above outputs, as the final data to the exposure time calculator 58.

As described above, since the mammary gland position identifier 56 selects a plurality of AEC sensors 42 to identify a mammary gland position using the average value or the median, it is possible to more accurately identify a distribution of a region of interest (mammary gland position). Specifically, by increasing the contrast in a mammary gland region (e.g. region R3 in FIG. 8A) or for each of mammary gland regions (e.g. regions R2, R4, R5 in FIG. 8B) of the obtained radiation image, it is possible to obtain an improved radiation image. Accordingly, in the case shown in FIG. 8A, contrast within one region R3 can be made high, and in the case shown in FIG. 8B, contrast between one region R2 and its adjacent regions R4, R5 can be made high. Thus, the entire radiation image of the breast 34 can be made clearer.

In the above embodiment, the mammary gland position identifier 56 selects the AEC sensor ch11 which outputs the minimum radiation dose after correction by the weighting coefficient allocator 60. However, the mammary gland position identifier 56 may select a plurality of AEC sensors which output the minimum radiation dose. In this case, they may be selected such that their actual outputs fall within ±20% of the average value or each of actual outputs of the plural AEC sensors, for example.

In the above embodiment, although an actual output range (threshold range) of the selected AEC sensors 42 is within ±20% of the actual output of the selected AEC sensor ch11, it may be within ±15%, for example, thereof. Also, an operator may optionally set the range via the display console panel 32.

After the mammary gland position identifier 56 has identified the mammary gland position, the exposure time calculator 58 calculates an exposure time in which to apply a radiation dose required to obtain appropriate radiation image information of the mammary gland region of the breast 34, as an exposure control condition, based on the radiation dose per unit time detected by the AEC sensor 42 at the mammary gland position.

Since the radiation X applied to the AEC sensors 42 is partly absorbed by the solid-state detector 38, the radiation dose per unit time detected by the AEC sensors 42 needs to be corrected into a radiation dose per unit time that reaches the detecting surface of the solid-state detector 38 in view of the attenuation of the radiation X caused by the solid-state detector 38.

The exposure time calculator 58 calculates an exposure time for the radiation X such that the integrated value of the radiation dose per unit time that reaches the detecting surface of the solid-state detector 38, as corrected in view of the above factors, and the exposure time will provide a radiation dose required to obtain appropriate radiation image information of the mammary gland region. The calculated exposure time is set as the exposure control condition in the radiation source controller 54.

Then, the mammographic system 10 starts to operate in the main exposure mode.

The radiation source controller 54 sets the tube current supplied to the radiation source 20 to a current for obtaining a radiation dose per unit time required in the main exposure mode. Then, when the operator operates the exposure switch 52, the radiation source 20 which is controlled by the tube current set by the radiation source controller 54 applies the radiation X to the breast 34. After the exposure time set as the exposure control condition has elapsed, the radiation source 20 stops applying the radiation X to the breast 34.

The radiation dose during the main exposure mode may be detected by one of the AEC sensors 42, e.g., the AEC sensor ch11, and its integrated value may be calculated. If the radiation dose of the radiation X exceeds an allowable level before the set exposure time elapses, then the radiation source controller 54 may control the radiation source 20 to stop applying the radiation X to the breast 34. Therefore, the subject 18 may be prevented in advance from being exposed to an excessive amount of the radiation X due to a failure of the mammographic system 10.

The radiation X that has passed through the breast 34 held between the compression plate 26 and the image capturing base 24 is applied to the solid-state detector 38 housed in the image capturing base 24. Now, radiation image information represented by the radiation X that has passed through the breast 34 is recorded in the solid-state detector 38. After the radiation image information of the breast 34 has been recorded, the reading light source 44 moves in the direction indicated by the arrow C (FIG. 3) along the solid-state detector 38 and applies reading light to the solid-state detector 38. In response to the applied reading light, the radiation image information recorded in the solid-state detector 38 is read into the radiation image forming unit 59, which forms a radiation image based on the radiation image information. The formed radiation image is then displayed on the display unit 61. In order to prepare the solid-state detector 38 for the capture of a next radiation image, the solid-state detector 38 from which the radiation image information has been read is irradiated with erasing light emitted from the erasing light source 40 to remove unwanted electric charges stored in the solid-state detector 38.

The display unit 61 may display the image of one of the AEC sensors 42, e.g., the AEC sensor ch11, corresponding to the mammary gland position identified by the mammary gland position identifier 56, in overlapping relation to the radiation image for the operator to confirm whether the mammary gland position identified by the mammary gland position identifier 56 is appropriate or not.

For subsequently capturing a left MLO image of the left breast 34, the arm 16 is turned a predetermined angle about the swing shaft 14 and set to a predetermined angular position. Then, the operator holds the left breast 34 between the image capturing base 24 and the compression plate 26. The mammographic system 10 then operates in the same manner as described above for capturing the right MLO image of the right breast 34.

Figure 9:
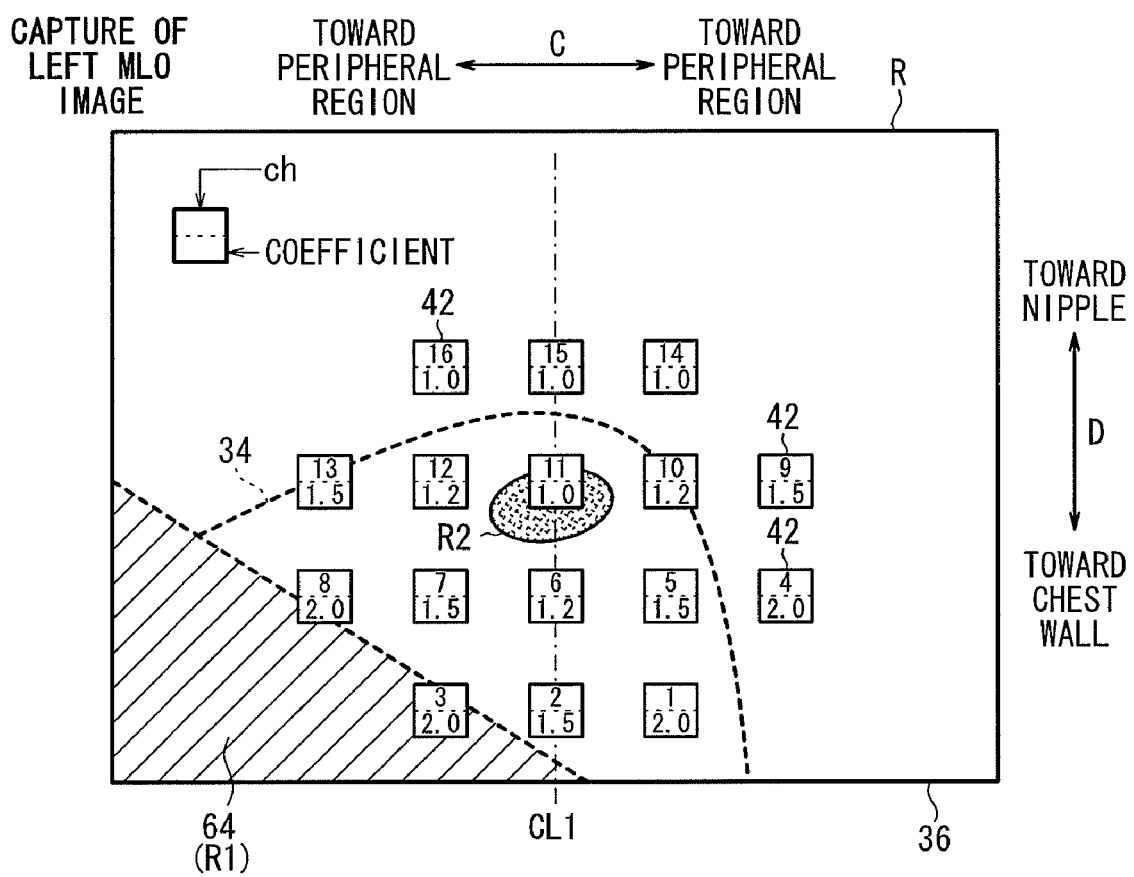
FIG. 9 is a schematic plan view showing the manner in which the breast is held on the image capturing base for capturing a left MLO image thereof.

When a left MLO image of the left breast 34 is to be captured, as shown in FIG. 9, the region R1 including the breast muscle 64 is positioned in symmetrical relation to the region R1 where the breast muscle 64 is positioned to capture the right MLO image, with respect to the central line CL1. The weighting coefficient allocator 60 multiplies the output signals from the AEC sensors 42 by weighting coefficients which are established such that the mammary gland position identifier 56 preferentially selects one of the AEC sensors 42 which is positioned more toward the center of the breast 34 than the peripheral region thereof and which is positioned more toward the nipple than the chest wall 36. Even though the region R1 is differently positioned for capturing a left MLO image of the left breast 34, the output signals from the AEC sensors ch3, ch8 overlapping the region R1 are largely corrected. Consequently, the mammary gland position identifier 56 is effectively prevented from erroneously selecting the positions of the AEC sensors 42 (the AEC sensors ch3, ch8 in FIG. 9) in the region R1 overlapping the breast muscle 64 as the mammary gland position (region of interest). Instead, the mammary gland position identifier 56 accurately detects one of the AEC sensors 42, i.e., the AEC sensor ch11 in FIG. 9, belonging to the region R2 where the mammary gland density is high. Accordingly, a left MLO image of the left breast 34 can be captured under the appropriate exposure control condition.

Depending on the size of the breast 34, the center of the breast 34 may not be held on the central line CL1 shown in FIG. 6. For example, if the breast 34 has a smaller size, the center of the breast 34 may be held on a central line CL2 which is shifted to the right from the central line CL1 in one of the directions indicated by the arrow C as shown in FIG. 10.

To process the output signals generated by the AEC sensors 42 when the center of the breast 34 is located on the central line CL2, the mammographic system 10 has a holding position selector switch (not shown) on the display console panel 32. The operator operates the holding position selector switch to select the central line CL2 and input a signal indicating that the center of the breast 34 on the image capturing base 24 is positioned on the central line CL2. Based on the signal from the holding position selector switch, the holding position identifier 62 (see FIG. 4) identifies the holding position of the breast 34 on the image capturing base 24, and supplies the identified holding position to the weighting coefficient allocator 60.

Figure 10:
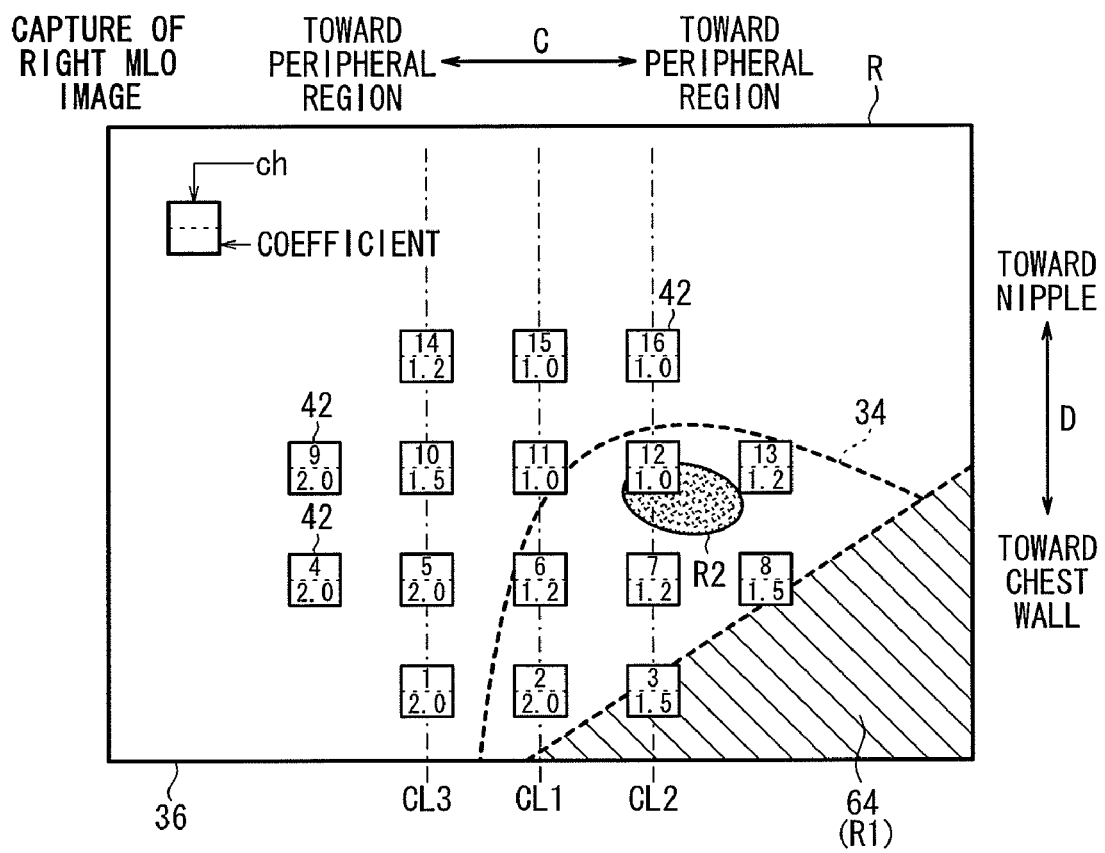
FIG. 10 is a schematic plan view showing the manner in which the breast is held in an off-center position on the image capturing base.

Based on the holding position information about the breast 34 from the holding position identifier 62, the weighting coefficient allocator 60 shifts the weighting coefficients set based on the central line CL1 shown in FIG. 10 to the weighting coefficients set based on the central line CL2. In other words, when the center of the breast 34 is shifted to the central line CL2, the weighting coefficients by which the output signals from the AEC sensors 42 are to be multiplied are shifted from the settings based on the central line CL1 to the settings based on the central line CL2. According to the settings based on the central line CL2, the weighting coefficients are established such that they are stepwise greater from those AEC sensors 42 (AEC sensors ch3, ch7, ch12, ch16) installed on the central line CL2 toward outer peripheral AEC sensors 42 in the directions indicated by the arrow C along the chest wall 36.

Therefore, even though the center of the breast 34 is shifted to the central line CL2, the mammary gland position identifier 56 can select one of the AEC sensors 42 whose output signal represents a minimum radiation dose among the output signals (radiation dose information) of the AEC sensors 42 which have been corrected by the weighting coefficient allocator 60, and reliably identify the position of the selected AEC sensor 42 as a mammary gland position (radiation dose measuring position).

Even if the center of the breast 34 is shifted to another central line CL3 (see FIG. 10), the weighting coefficients may be shifted to the settings based on the central line CL3, in the same manner as when the center of the breast 34 is shifted to the central line CL2.

As described above, the weighting coefficient allocator 60 includes a function as a weighting coefficient shifting means for shifting the weighting coefficients by which the output signals from the AEC sensors 42 are to be multiplied, to different settings in the directions indicated by the arrow C along the chest wall 36, depending on the holding position of the breast 34 which has been identified by the holding position identifier 62.

In the mammographic system 10 according to the present embodiment, the holding position identifier 62 may identify the holding position of the breast 34 according to any of various processes, i.e., first through sixth processes to be described below, rather than based on the signal input from the holding position selector switch.

Those first through six processes for identifying the holding position of the breast 34 with the holding position identifier 62 will be described below with reference to FIGS. 11 through 16.

Figure 11:
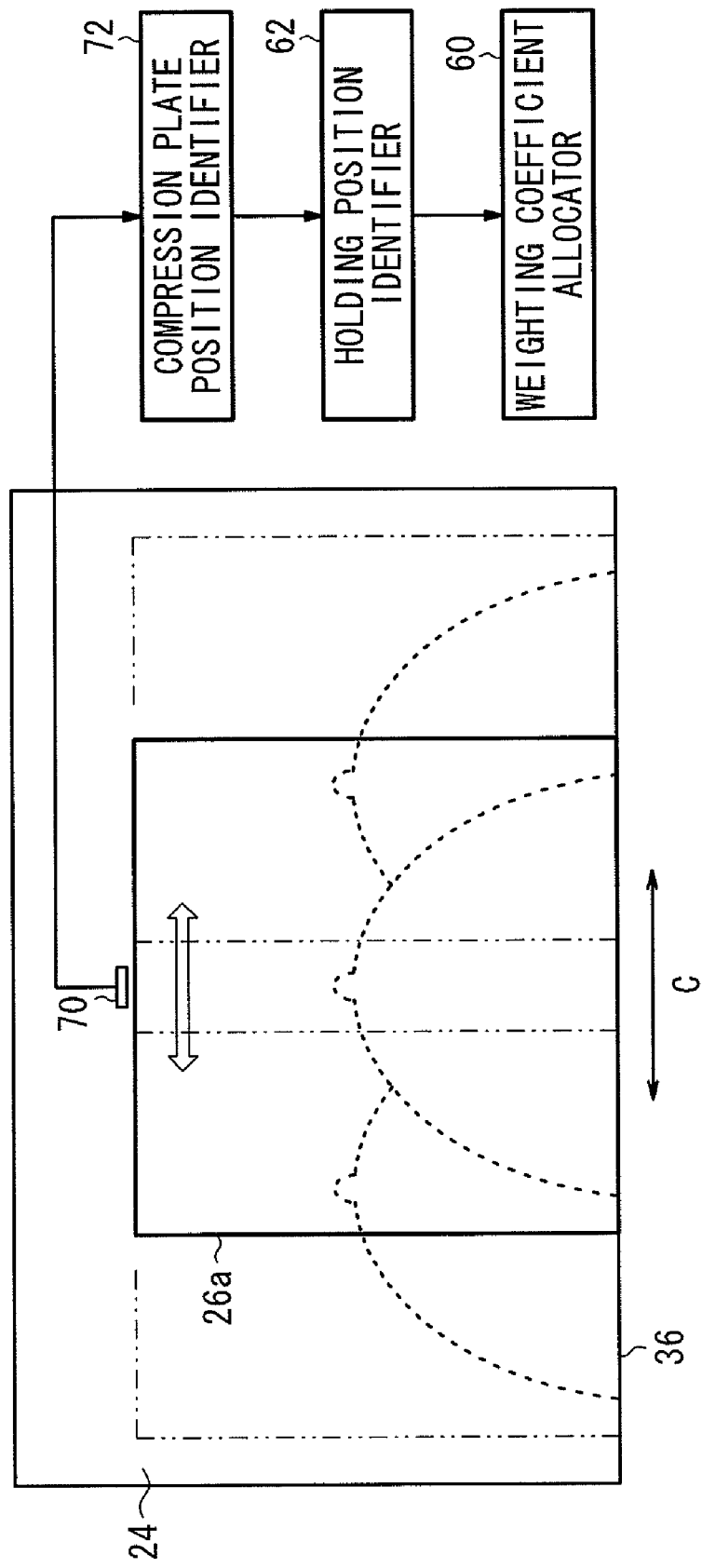
FIG. 11 is a view, partly in block form, illustrative of a first process of identifying a breast holding position.

FIG. 11 is a view, partly in block form, illustrative of the first process of identifying the holding position of the breast 34. As shown in FIG. 10, the breast 34 is secured to the image capturing base 24 by a compression plate 26a movable in the directions indicated by the arrow C. Depending on the size of the breast 34, the compression plate 26a is moved to an appropriate position for reliably securing the breast 34. The position of the compression plate 26a, i.e., the distance over which the compression plate 26a has moved, is detected by a compression plate position detector 70. A compression plate position identifier (compression plate position identifying means) 72 identifies the position of the compression plate 26a based on compression plate position information detected by the compression plate position detector 70.

The holding position identifier 62 identifies the holding position of the breast 34 based on the position of the compression plate 26a which has been identified by the compression plate position identifier 72, and supplies the identified holding position to the weighting coefficient allocator 60.

Figure 12:
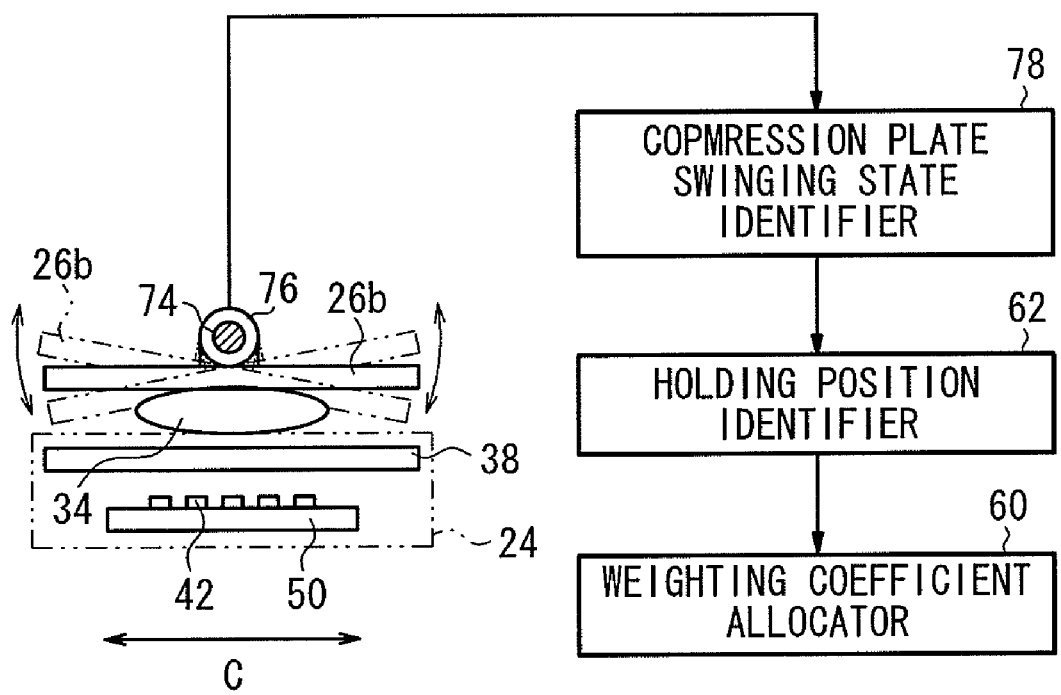
FIG. 12 is a view, partly in block form, illustrative of a second process of identifying a breast holding position.

FIG. 12 is a view, partly in block form, illustrative of the second process of identifying the holding position of the breast 34. As shown in FIG. 11, the breast 34 is secured to the image capturing base 24 by a compression plate 26b which is swingably supported by a swing shaft 74 mounted on the center of the compression plate 26b in the directions indicated by the arrow C. The swing shaft 74 is associated with a compression plate swinging state detector 76 which detects one or more of a plurality of swinging states of the compression plate 26b, i.e., a swinging direction, a swinging force (a torque in the swinging direction with the breast 34 secured to the image capturing base 24), and a swinging angle while the compression plate 26b is securing the breast 34 to the image capturing base 24. A compression plate swinging state identifier (compression plate swinging state identifying means) 78 identifies the swinging state of the compression plate 26b based on the information on the swinging state of the compression plate 26b which has been detected by the compression plate swinging state detector 76.

The holding position identifier 62 identifies the holding position of the breast 34 based on the swinging state of the compression plate 26b which has been identified by the compression plate swinging state identifier 78, and supplies the identified holding position to the weighting coefficient allocator 60. Specifically, if the holding position of the breast 34 is displaced outwardly from the center of the compression plate 26b, then since the compression plate 26b swings depending on the displacement of the holding position of the breast 34. Accordingly, the holding position identifier 62 can identify the holding position of the breast 34 from the swinging state of the compression plate 26b.

Figure 13:
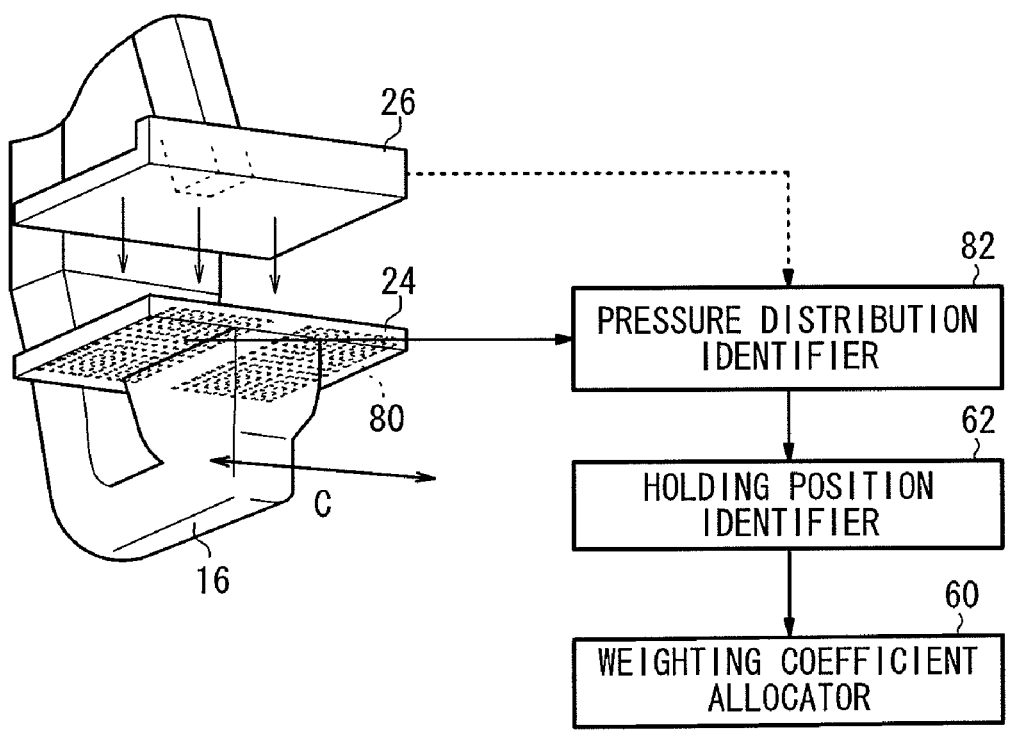
FIG. 13 is a view, partly in block form, illustrative of a third process of identifying a breast holding position.

FIG. 13 is a view, partly in block form, illustrative of the third process of identifying the holding position of the breast 34. As shown in FIG. 12, a pressure detector 80 is incorporated in the image capturing base 24 which is pressed by the compression plate 26 with the breast 34 secured thereby. The pressure detector 80 detects pressures applied from the compression plate 26 to the image capturing base 24. The pressure detector 80 may comprise a pressure-sensitive sheet, for example. A pressure distribution identifier (pressure distribution identifying means) 82 identifies a pressure distribution developed over the image capturing base 24 based on the pressure information detected by the pressure detector 80.

The holding position identifier 62 identifies the holding position of the breast 34 based on the pressure distribution over the image capturing base 24 which has been identified by the pressure distribution identifier 82, and supplies the identified holding position to the weighting coefficient allocator 60. Specifically, inasmuch as the pressure distribution over the image capturing base 24 is acquired depending on the holding position of the breast 34, the holding position of the breast 34 can be identified by identifying and analyzing the pressure distribution. The pressure detector 80 may be incorporated in the compression plate 26.

Figure 14:
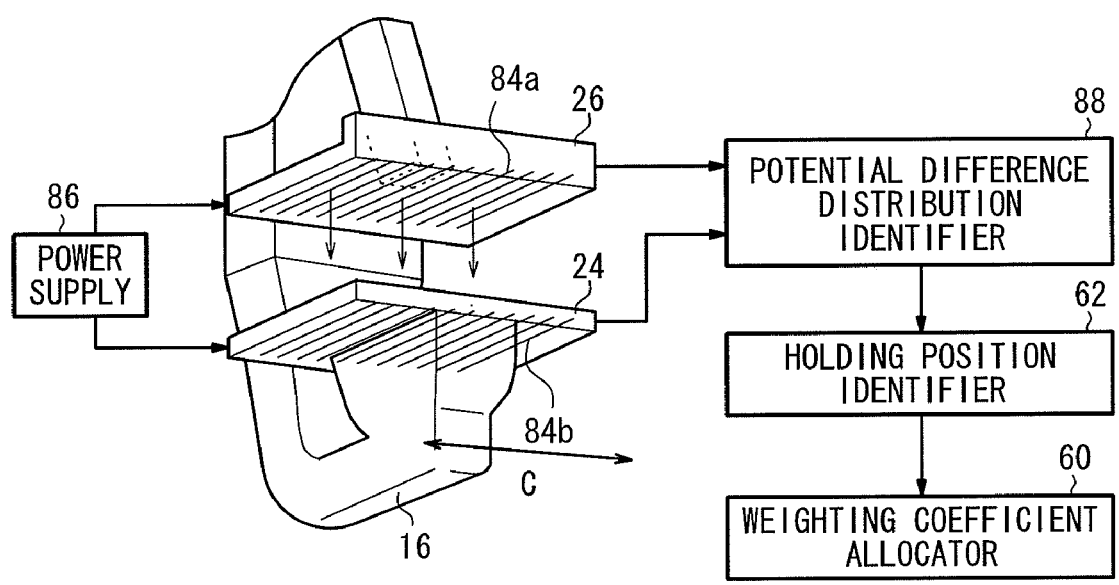
FIG. 14 is a view, partly in block form, illustrative of a fourth process of identifying a breast holding position.

FIG. 14 is a view, partly in block form, illustrative of the fourth process of identifying the holding position of the breast 34. As shown in FIG. 13, the compression plate 26 and the image capturing base 24 incorporate respective electrodes (transparent electrodes) 84*a*, 84*b* therein. A power supply 86 supplies a weak current between the electrodes 84*a*, 84*b* through the breast 34 held between the compression plate 26 and the image capturing base 24. A potential difference distribution identifier (potential difference distribution identifying means) 88 detects the potential difference (voltage) between the electrodes 84*a*, 84*b* and identifies a potential difference distribution in the directions indicated by the arrow C. Specifically, each of the electrodes 84*a*, 84*b* comprises an array of narrow electrode strips extending in a direction perpendicular to the directions indicated by the arrow C along the chest wall 36 of the subject 18. The narrow electrode strips of the electrodes 84*a*, 84*b* make up a plurality of electrode strip pairs. The potential difference distribution identifier 88 detects potential differences between the electrode strip pairs whose electrode strips face each other across the breast 34, and acquires a potential difference distribution in the directions indicated by the arrow C.

The holding position identifier 62 identifies the holding position of the breast 34 based on the potential difference distribution identified by the potential difference distribution identifier 88, and supplies the identified holding position to the weighting coefficient allocator 60. Specifically, a potential difference is developed between the electrode strips of the electrodes 84*a*, 84*b* which are held in contact with the breast 34 and no potential difference is developed between the electrode strips of the electrodes 84*a*, 84*b* which are held out of contact with the breast 34. Therefore, the holding position of the breast 34 can be identified by identifying a distribution of such potential differences.

Figure 15:
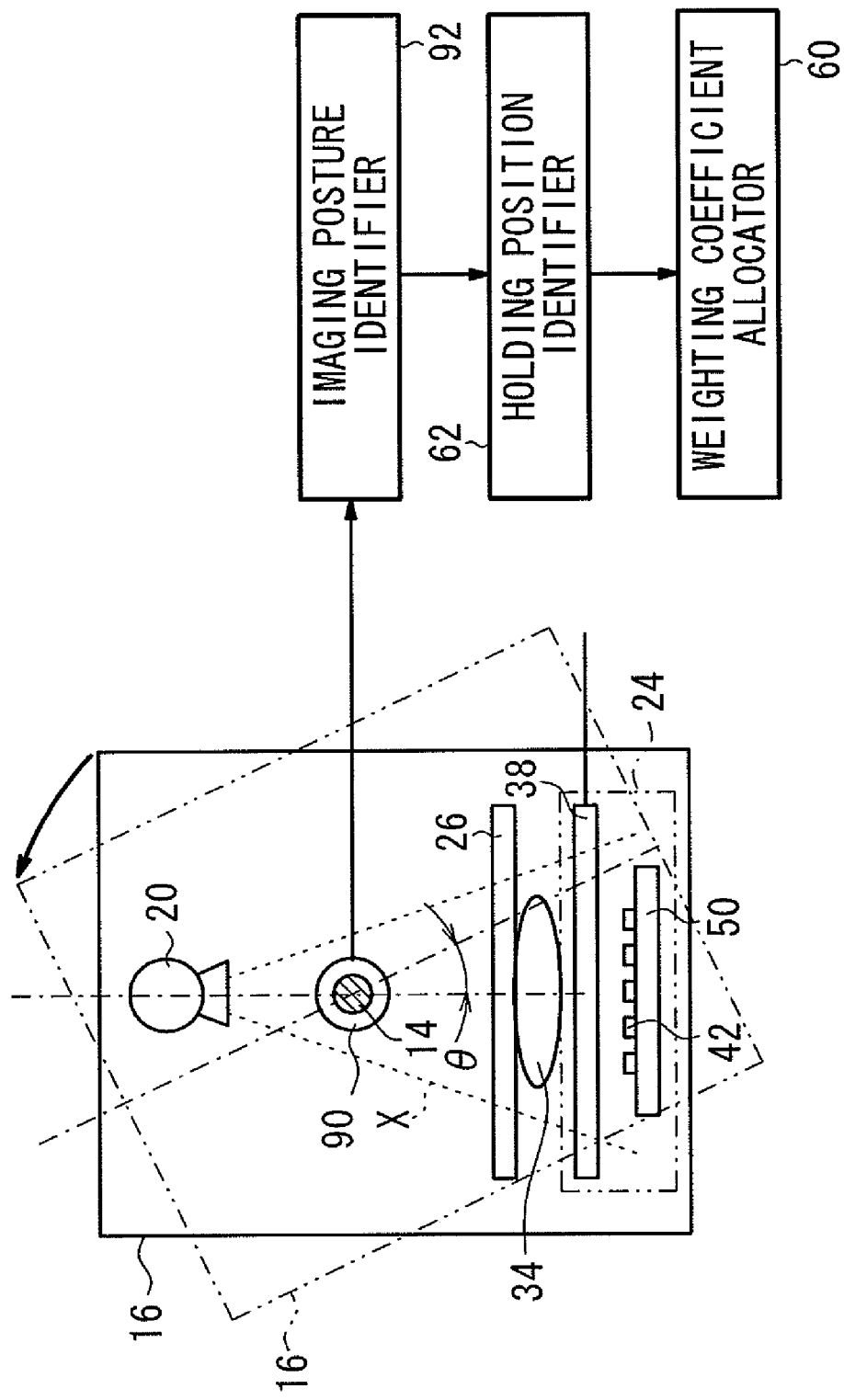
FIG. 15 is a view, partly in block form, illustrative of a fifth process of identifying a breast holding position.

FIG. 15 is a view, partly in block form, illustrative of the fifth process of identifying the holding position of the breast 34. As shown in FIG. 14, the swing shaft 14 connected to the arm 16 which supports the compression plate 26 and the image capturing base 24 is associated with a rotational angle detector 90 for detecting a rotational angle θ and a rotating direction of the swing shaft 14, i.e., the arm 16. An imaging posture identifier (imaging posture identifying means) 92 identifies an imaging posture of the breast 34, i.e., the angular position of the arm 16 and the imaging direction of the breast 34, based on the rotational angle θ and the rotating direction of the arm 16 which are detected by the rotational angle detector 90. The rotational angle detector 90 may comprise a potentiometer or an encoder.

The holding position identifier 62 identifies (estimates) the holding position of the breast 34 from stored map data in various angular positions and various imaging directions, for example, based on the imaging posture of the breast 34, i.e., the angular position of the arm 16 and the imaging direction of the breast 34, which have been identified by imaging posture identifier 92, and supplies the identified holding position to the weighting coefficient allocator 60.

Figure 16:
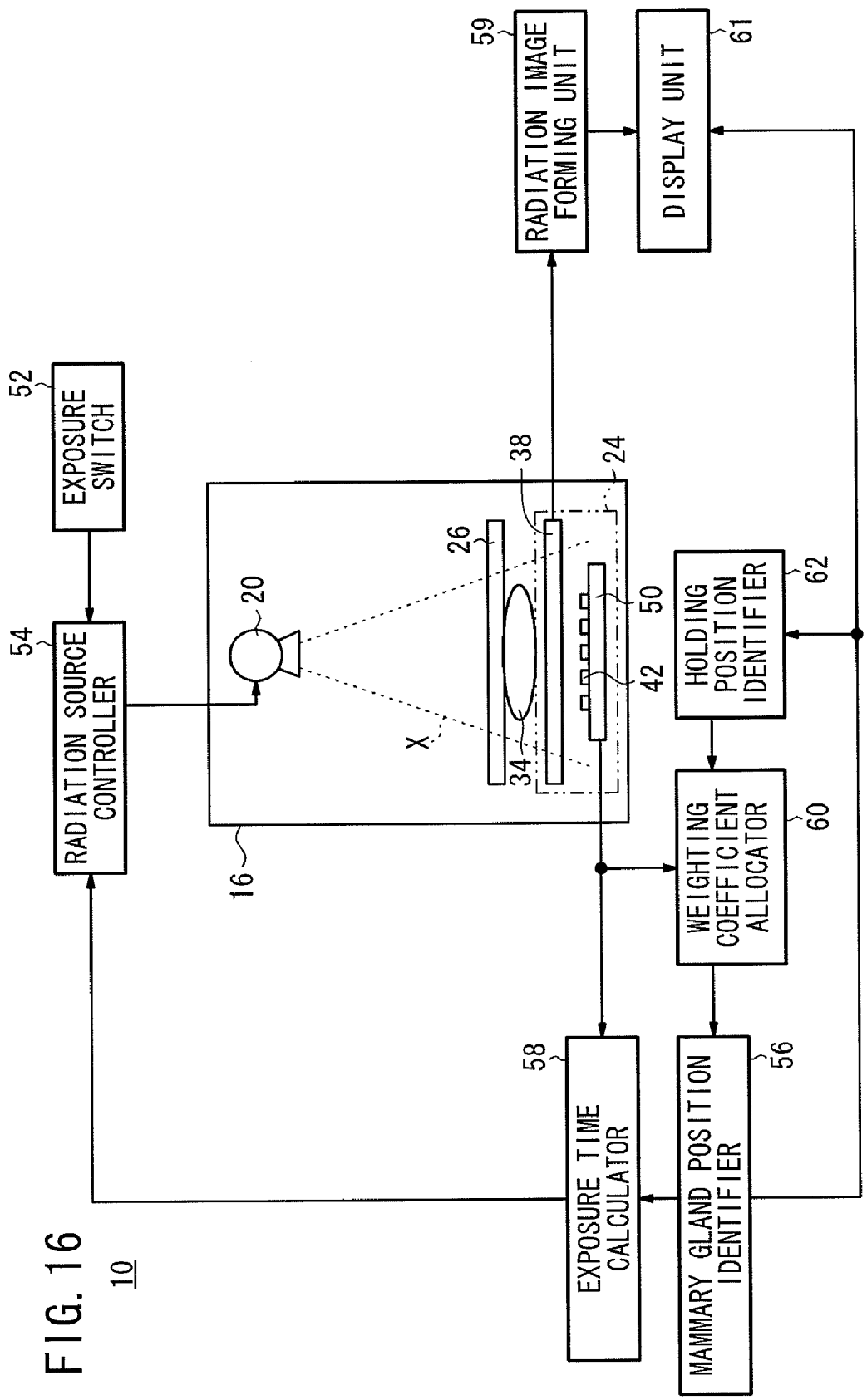
FIG. 16 is a view, partly in block form, illustrative of a sixth process of identifying a breast holding position.

FIG. 16 is a view, partly in block form, illustrative of the sixth process of identifying the holding position of the breast 34. For identifying the holding position of the breast 34, the holding position identifier 62 first supplies the weighting coefficient allocator 60 with an instruction not to multiply the output signals from the AEC sensors 42 by respective weighting coefficients. When the radiation X is applied from the radiation source 20 to the image capturing base 24, the output signals from the AEC sensors 42 are supplied to the mammary gland position identifier 56 without being multiplied by the weighting coefficients. The mammary gland position identifier 56 generates output signal distribution information representing a distribution of the output signals from the AEC sensors 42, and supplies the output signal distribution information to the holding position identifier 62. Based on the output signal distribution information from the mammary gland position identifier 56, the holding position identifier 62 recognizes the shape of the breast 34 thereby to identify the holding position of the breast 34, and supplies the identified holding position to the weighting coefficient allocator 60.

Various changes and modifications may be made to the illustrated embodiments.

For example, in the above embodiments, the solid-state detector (image sensor) 38 and the AEC sensors (radiation dose information detectors) 42 are separate from each other. If the image sensor comprises a TFT image sensor, then parts of the image sensor may be used as radiation dose information detectors. In this case, the radiation dose information detectors may be provided by the image sensor.

In the above embodiments, the radiation image capturing apparatus incorporates the solid-state detector 46 therein. However, the radiation image capturing apparatus may instead incorporate a stimulable phosphor panel detachably mounted in the image capturing base 24 or a solid-state radiation detector for directly converting an applied radiation into an image without the need for the reading light source 44.

The radiation image capturing apparatus according to the present invention is not limited to the mammographic system according to the illustrated embodiment, but is also applicable to a radiation image capturing apparatus for capturing an image of another region of the subject.

The weighting coefficients (see FIG. 6) described in the above embodiments may be changed depending on apparatus and methods to which the present invention is applicable, and the number of installed AEC sensors may also be changed.

In the above embodiments, when the holding position of the breast 34 is displaced and hence the weighting coefficients need to be shifted, the maximum value (2.0 in the illustrated embodiments) of the weighting coefficients is fixed, i.e., the weighting coefficients for both the AEC sensors ch4, ch5 are 2.0 as shown in FIG. 10. However, the weighting coefficient for the AEC sensor ch5 may be set to 2.0 and the weighting coefficient for the AEC sensor ch4 which is located outwardly of the AEC sensor ch5 may be set to 2.5.

Although certain preferred embodiments of the present invention have been shown and described in detail, it should be understood that various changes and modifications may be made therein without departing from the scope of the appended claims.

What is claimed is:

1. A method of controlling a radiation image capturing apparatus for capturing a radiation image of a subject, comprising the steps of:

applying a radiation from a radiation source to a region to be imaged of the subject;

detecting a dose of the radiation which has passed through said region to be imaged at a plurality of radiation dose measuring positions;

multiplying respective pieces of radiation dose information measured at said radiation dose measuring positions by respective weighting coefficients depending on said radiation dose measuring positions for selecting one or more of said radiation dose measuring positions based on the radiation dose information multiplied by said weighting coefficients;

determining an exposure control condition for the radiation from said radiation source based on said radiation dose information measured at the selected one or more radiation dose measuring positions; and wherein said region to be imaged comprises a breast of the subject, and said step of multiplying respective pieces of the radiation dose information comprises the step of multiplying the pieces of the radiation dose information by weighting coefficients established to preferentially select said one or more of said radiation dose measuring positions which are closer to the center of the breast than to the peripheral region thereof along the chest wall of the subject.

2. A method according to claim 1, wherein said region to be imaged comprises a breast of the subject, and said step of multiplying respective radiation dose information comprises the step of multiplying the radiation dose information by weighting coefficients established to preferentially select said one or more of said radiation dose measuring positions which are closer to the nipple of the breast than to the chest wall of the subject.

3. A method according to claim 1, wherein the weighting coefficients by which the pieces of the radiation dose information are to be multiplied are established to preferentially select said one or more of said radiation dose measuring positions which are closer to the nipple of the breast than to the chest wall of the subject.

4. A method according to claim 3, further comprising the step of:
shifting the weighting coefficients by which the pieces of the radiation dose information are to be multiplied along the chest wall of the subject depending on a holding position of the breast.

5. A method according to claim 4, further comprising the step of:
identifying the holding position of the breast by recognizing a shape of the breast based on the pieces of the radiation dose information measured at said radiation dose measuring positions.

6. A method according to claim 1, further comprising the step of:
shifting the weighting coefficients by which the pieces of the radiation dose information are to be multiplied along the chest wall of the subject depending on a holding position of the breast.

7. A method according to claim 6, further comprising the step of:
identifying the holding position of the breast by recognizing a shape of the breast based on the pieces of the radiation dose information measured at said radiation dose measuring positions.

8. A method of controlling a radiation image capturing apparatus for capturing a radiation image of a subject, comprising the steps of:
applying a radiation from a radiation source to a region to be imaged of the subject;
detecting a dose of the radiation which has passed through said region to be imaged at a plurality of radiation dose measuring positions;
multiplying respective pieces of radiation dose information measured at said radiation dose measuring positions by respective weighting coefficients depending on said radiation dose measuring positions for selecting one or more of said radiation dose measuring positions based on the radiation dose information multiplied by said weighting coefficients; and determining an exposure control condition for the radiation from said radiation source based on said radiation dose information measured at the selected one or more radiation dose measuring positions, wherein said step of multiplying respective pieces of the radiation dose information comprises:

a first step of multiplying respective pieces of radiation dose information measured at said radiation dose measuring positions by respective weighting coefficients depending on said radiation dose measuring positions for selecting one or more of predetermined radiation dose measuring positions; and a second step of comparing the multiplied radiation dose information with radiation dose information before being multiplied in said first step, for selecting one or more of radiation dose measuring positions having radiation dose information within a predetermined range, and wherein said step of determining the exposure control condition for the radiation comprises the step of determining the exposure control condition for the radiation from said radiation source based on respective pieces of radiation dose information at respective radiation dose measuring positions that have been selected in said first step and said second step.

9. A method according to claim 8, wherein said predetermined range in said second step is variable.

10. An apparatus for capturing a radiation image, for use as a mammographic system for imaging a breast of the subject as said region to be imaged, comprising:
a radiation source for applying a radiation to a region to be imaged of a subject;
a radiation dose information detector for detecting a dose of the radiation which has passed through said region to be imaged at a plurality of radiation dose measuring positions, and acquiring respective pieces of radiation dose information for exposure control at said radiation dose measuring positions;
weighting coefficient allocating means for multiplying the respective pieces of the radiation dose information measured at said radiation dose measuring positions by respective weighting coefficients depending on said radiation dose measuring positions;
measuring position selecting means for selecting one or more of said radiation dose measuring positions; and
radiation source control means for controlling the dose of the radiation emitted from said radiation source based on the pieces of the radiation dose information measured at the one or more radiation dose measuring positions which are selected by said measuring position selecting means; and
an image capturing base housing said radiation dose information detector therein; and
holding position identifying means for identifying a holding position of the breast on said image capturing base;
wherein said weighting coefficient allocating means comprises weighting coefficient shifting means for shifting the weighting coefficients by which the pieces of the radiation dose information are to be multiplied along the chest wall of the subject depending on the holding position of the breast which is identified by said holding position identifying means.

11. An apparatus according to claim 10, further comprising:
- a compression plate for compressing the breast securely to said image capturing base, said compression plate being movable at least along the chest wall of the subject; and
- compression plate position identifying means for identifying a position of said compression plate;
- wherein said holding position identifying means identifies the holding position of the breast on said image capturing base based on the position of said compression plate which is identified by said compression plate position identifying means.

12. An apparatus according to claim 10, further comprising:
- a compression plate for compressing the breast securely to said image capturing base, said compression plate being swingable in directions toward and away from said image capturing base; and
- compression plate swinging state identifying means for identifying a swinging state of said compression plate which represents one or more of a swinging direction, a swinging force, and a swinging angle of said compression plate;
- wherein said holding position identifying means identifies the holding position of the breast on said image capturing base based on the swinging state of said compression plate which is identified by said compression plate swinging state identifying means.

13. An apparatus according to claim 10, further comprising:
- a compression plate for compressing the breast securely to said image capturing base;
- a pressure detector for detecting pressures applied from said compression plate to said image capturing base; and
- pressure distribution identifying means for identifying a distribution of the pressures detected by said pressure detector;
- wherein said holding position identifying means identifies the holding position of the breast on said image capturing base based on said distribution of the pressures which is identified by said pressure distribution identifying means.

14. An apparatus according to claim 10, further comprising:
- a compression plate for compressing the breast securely to said image capturing base;
- a pair of electrodes mounted respectively on said image capturing base and said compression plate;
- a power supply for passing a current between said electrodes; and
- potential difference distribution identifying means for identifying a distribution of potential differences between said electrodes when said power supply passes the current between said electrodes while the breast is being held between said image capturing base and said compression plate;
- wherein said holding position identifying means identifies the holding position of the breast on said image capturing base based on the distribution of potential differences which is identified by said potential difference distribution identifying means.

15. An apparatus according to claim 10, further comprising:
- an angularly movable arm securing said radiation source and said image capturing base to each other in confronting relation to each other with the breast interposed therebetween; and
- imaging posture identifying means for identifying an imaging posture of the breast based on a rotational angle or a rotating direction of said arm;
- wherein said holding position identifying means identifies the holding position of the breast on said image capturing base based on the imaging posture of the breast which is identified by said imaging posture identifying means.

* * * * *